US010064554B2

(12) United States Patent
Floyd et al.

(10) Patent No.: US 10,064,554 B2
(45) Date of Patent: Sep. 4, 2018

(54) FIBER OPTIC FLOW AND OXYGENATION MONITORING USING DIFFUSE CORRELATION AND REFLECTANCE

(71) Applicants: The Trustees of The University of Pennsylvania, Philadelphia, PA (US); The Research Foundation of State University of New York, Albany, NY (US)

(72) Inventors: Thomas F. Floyd, Media, PA (US); Arjun G Yodh, Merion, PA (US); Rickson C. Mesquita, Campinas (BR)

(73) Assignees: The Trustees of the University of Pennsylvania, Philadelphia, PA (US); The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 14/364,533

(22) PCT Filed: Dec. 14, 2012

(86) PCT No.: PCT/US2012/069626
§ 371 (c)(1),
(2) Date: Jun. 11, 2014

(87) PCT Pub. No.: WO2013/090658
PCT Pub. Date: Jun. 20, 2013

(65) Prior Publication Data
US 2014/0343384 A1    Nov. 20, 2014

Related U.S. Application Data

(60) Provisional application No. 61/570,349, filed on Dec. 14, 2011.

(51) Int. Cl.
*A61B 5/1455*   (2006.01)
*A61B 5/00*   (2006.01)
(Continued)

(52) U.S. Cl.
CPC .......... *A61B 5/0084* (2013.01); *A61B 5/0075* (2013.01); *A61B 5/0261* (2013.01);
(Continued)

(58) Field of Classification Search
None
See application file for complete search history.

(56) References Cited

U.S. PATENT DOCUMENTS 5,024,226 A    6/1991  Tan
5,396,880 A    3/1995  Kagan
(Continued)

FOREIGN PATENT DOCUMENTS

WO    WO 2006/097910    9/2006
WO    WO 2009/116029    9/2009
(Continued)

OTHER PUBLICATIONS

Baldwin, B.A., "The Anatomy of the Arterial Supply to the Cranial Regions of the Sheep and Ox", Am J Anat, 1964, 115, 101-107.
(Continued)

*Primary Examiner* — Eric Winakur
*Assistant Examiner* — Marjan Fardanesh
(74) *Attorney, Agent, or Firm* — Baker & Hostetler LLP

(57) ABSTRACT

Disclosed are fiber optic devices and related methods that allow for measurement of blood flow and oxygenation in real time. These devices have particular application to the spinal cord. Such devices have applicability in, for example, the care of military members sustaining combatant and noncombatant spinal injuries, as well as to civilians. The devices also have utility in the acute and subacute manage-
(Continued)

Linear Arrayed Fiber Optic Spinal Cord Sensor ment of spine trauma, enhancing the efficacy of interventions aimed at the prevention of secondary ischemic injury, and ultimately improving neurologic outcome.

34 Claims, 18 Drawing Sheets

(51) Int. Cl.
*A61B 5/026* (2006.01)
*A61B 5/1459* (2006.01)
*A61B 5/0275* (2006.01)

(52) U.S. Cl.
CPC ........ *A61B 5/1459* (2013.01); *A61B 5/14552* (2013.01); *A61B 5/0275* (2013.01)

(56) References Cited

U.S. PATENT DOCUMENTS

| | | | |
|---|---|---|---|
| 6,341,036 | B1 | 1/2002 | Tearney et al. |
| 7,515,948 | B1 | 4/2009 | Balberg et al. |
| 7,541,602 | B2 | 6/2009 | Metzger et al. |
| 7,613,504 | B2 | 11/2009 | Rowe |
| 8,082,015 | B2 | 12/2011 | Yodh et al. |
| 8,108,022 | B2 | 1/2012 | Balberg et al. |
| 8,126,524 | B2 | 2/2012 | Balberg et al. |
| 8,143,605 | B2 | 3/2012 | Metzger et al. |
| 2002/0156513 | A1 | 10/2002 | Borkan |
| 2004/0186359 | A1 | 9/2004 | Beaudoin et al. |
| 2005/0043606 | A1 | 2/2005 | Pewzner et al. |
| 2006/0264747 | A1 | 11/2006 | Pesach et al. |
| 2009/0069673 | A1* | 3/2009 | Tapalian ............... A61B 5/0066 600/425 |
| 2010/0105998 | A1 | 4/2010 | Benni |
| 2011/0196241 | A1* | 8/2011 | Froehlich ............. A61B 5/6833 600/476 |
| 2011/0251494 | A1 | 10/2011 | Hendriks et al. |
| 2012/0150014 | A1 | 6/2012 | Metzger et al. |
| 2012/0184830 | A1 | 7/2012 | Balberg et al. |

FOREIGN PATENT DOCUMENTS

| | | |
|---|---|---|
| WO | WO 2010/004554 | 1/2010 |
| WO | WO 2013/090658 | 6/2013 |

OTHER PUBLICATIONS

Banerjea et al, "Co-Occurring Medical and Mental Illness and Substance Use Disorders Among Veteran Clinic Users With Spinal Cord Injury Patients With Complexities", Spinal Cord, May 5, 2009, 47(11), 789-795.
Biglioli et al, Upper and Lower Spinal Cord Blood Supply: The Continuity of the Anterior Spinal Artery and the Relevance of the Lumbar Arteries. J. Thorac. Cardiovasc. Surg., Apr. 2004, 127(4), 1188-1192.
Boas et al, "Scattering and Imaging with Diffusing Temporal Field Correlations", Phys. Rev. Lett., Aug. 28, 1995, 75(9), 1855-1858.
Bockler et al, "Spinal Cord Ischemia After Endovascular Repair of the Descending Thoracic Aorta in a Sheep Model", Eur. J. Vasc. Endovasc. Surg., Oct. 2007, 34(4), 461-9.
Bricknell et al, "Military Parachuting Injuries: A Literature Review", Occup. Med. (Lond), 1999, 49(1), 17-26.
Buckley et al, "Cerebral Hemodynamics in Preterm Infants During Positional Intervention Measured With Diffuse Correlation Spectroscopy and Transcranial Doppler Ultrasound". Opt. Express, Jul. 20, 2009, 17(15), 12571-81.
Buxton, N., "The Military Medical Management of Missile Injury to the Spine: A Review of the Literature and Proposal of Guidelines", J R Army Med. Corps, 2001, 147(2), 168-72.
Carp et al, "Validation of Diffuse Correlation Spectroscopy Measurements of Rodent Cerebral Blood Flow With Simultaneous Arterial Spin Labeling MRI; towards MRI-Optical Continuous Cerebral Metabolic Monitoring", Biomed. Opt. Express, Sep. 1, 2010, 1(2), 553-565.
Cermik et al, "Assessment of Regional Blood Flow in Cerebral Motor and Sensory Areas in Patients With Spinal Cord Injury", Brain Res, 2006, 1109(1), 54-9.
Coselli et al, "Open Surgical Repair of 2286 Thoracoabdominal Aortic Aneurysms", Ann Thorac. Surg., Feb. 2007, 83(2), S862-4; discussion S890-2.
Costa et al, "Somatosensory- and Motor-Evoked Potential Monitoring During Spine and Spinal Cord Surgery", Spinal Cord, 2007, 45(1), 86-91, Published Online: May 2, 2006.
Daudel et al, "Effects of Thoracic Epidural Anesthesia on Hemodynamics and Global Oxygen Transport in Ovine Endotoxemia", Shock, 2006, 26(6), 615-619.
De Visscher et al, "NIRS Mediated CBF Assessment: Validating the Indocyanine Green Bolus Transit Detection by Comparison With Coloured Microsphere Flowmetry", Adv. Exp. Med. Biol., 2003, 540, 37-45.
Deiner, S.,"Highlights of Anesthetic Considerations for Intraoperative Neuromonitoring", Semin. Cardiothorac Vasc. Anesth., 2010, 14(1), 51-3.
Deletis, V. and F. Sala, "Intraoperative Neurophysiological Monitoring of the Spinal Cord During Spinal Cord and Spine Surgery: A Review Focus on the Corticospinal Tracts", Clin. Neurophysiol., 2008, 119(2), 248-64.
Deletis et al, "Neurophysiological Mechanisms Underlying Motor Evoked Potentials in Anesthetized Humans. Part 1. Recovery Time of Corticospinal Tract Direct Waves Elicited by Pairs of Transcranial Electrical Stimuli", Clin. Neurophysiol, 2001, 112(3), 438-44.
Deletis et al, "Neurophysiological Mechanisms Underlying Motor Evoked Potentials in Anesthetized Humans. Part 2. Relationship Between Epidurally and Muscle Recorded MEPs in Man", Clin. Neurophysiol, 2001, 112(3), 445-52.
Dommisse, G.F., "The Blood Supply of the Spinal Cord. A Critical Vascular Zone in Spinal Surgery", J. Bone Joint Surg. Br., 1974, 56(2), 225-35.
Duhamel et al, "Mouse Lumbar and Cervical Spinal Cord Blood Flow Measurements by Arterial Spin Labeling: Sensitivity Optimization and First Application", Magn. Reson. Med., 2009, 62(2), 430-439, Published Online: Jun. 12, 2009.
Durduran et al, "Transcranial Optical Monitoring of Cerebrovascular Hemodynamics in Acute Stroke Patients", Opt Express, Mar. 2, 2009, 17(5), 3884-902.
Durduran et al, "Diffuse optics for tissue monitoring and tomography", Rep. Prog. Phys., Jun. 2, 2010, 73, 076701.
Duz et al, "Evaluation of Spinal Missile Injuries With Respect to Bullet Trajectory, Surgical Indications and Timing of Surgical Intervention: A New Guideline", Spine (Phila Pa 1976), Sep. 15, 2008, 33(20), E746-53.
Estrera et al, "Cerebrospinal Fluid Drainage During Thoracic Aortic Repair: Safety and Current Management", Ann. Thorac. Surg., Jul. 2009, 88(1), 9-15; discussion 15.
Etz et al, "Spinal Cord Blood Flow and Ischemic Injury After Experimental Sacrifice of Thoracic and Abdominal Segmental Arteries", Eur. J. Cardiothorac. Surg., 2008, 33(6), 1030-1038.
Eucker et al, "Development of a Fluorescent Microsphere Technique for Rapid Histological Determination of Cerebral Blood Flow", Brain Res, Apr. 22, 2010, 1326,128-34.
Figaji et al, "Brain Tissue Oxygen Tension Monitoring in Pediatric Severe Traumatic Brain Injury. Part 1: Relationship with outcome", Childs Nerv. Syst., 2009, 25(10), 1325-33, Published Online: Feb. 13, 2009.
Findley et al, "Excess Mortality Associated With Mental Illness and Substance Use Disorders Among Veteran Clinic Users With Spinal Cord Injury", Disabil. Rehabil., 2011, 33(17-18), 1608-1615.
French et al, "Health Care Costs for Patients With Chronic Spinal Cord Injury in the Veterans Health Administration", J. Spinal Cord. Med., 2007, 30(5), 477-81.

(56) References Cited

OTHER PUBLICATIONS

Furlan et al, "Timing of Decompressive Surgery of Spinal Cord After Traumatic Spinal Cord Injury: An Evidence-Based Examination of Pre-Clinical and Clinical Studies", J. Neurotrauma, 2011, 28(8), 1371-99.
Glorioso et al, "Military Free Fall Training Injuries", Mil. Med., Jul. 1999, 164(7), 526-530.
Grady et al, "Neurologic Complications After Placement of Cerebrospinal Fluid Drainage Fiber Optic Probes and Needles in Anesthetized Patients: Implications for Regional Anesthesia. Mayo Perioperative Outcomes Group", Anesth. Analg., Feb. 1999, 88(2), 388-92.
Gupta et al, "Advances in the Management of Spinal Cord Injury", J. Am. Acad. Orthop. Surg., Apr. 2010, 18(4), 210-22.
Hauret et al, "Frequency and Causes of Nonbattle Injuries Air Evacuated From Operations Iraqi Freedom and Enduring Freedom, U.S. Army, 2001-2006". Am. J. Prev. Med., Jan. 2010, 38(1 Suppl), S94-107.
Holmes et al, "Epidemiology of Thoracolumbar Spine Injury in Blunt Trauma", Acad. Emerg. Med., Sep. 2001, 8(9), 866-72.
Hong et al, "False negative and positive motor evoked potentials in one patient: is single motor evoked potential monitoring reliable method?: a case report and literature review", Spine (Phila Pa 1976), 2010, 35(18), E912-6.
Hooper et al, "Understanding the Effect of Deployment on the Risk of Fatal Motor Vehicle Crashes: A Nested Case-Control Study of Fatalities in Gulf War Era Veterans", 1991-1995. Accid. Anal. Prev., May 2006, 38(3), 518-525.
Horlocker et al, "Retrospective Review of 4767 Consecutive Spinal Anesthetics: Central Nervous System Complications. Perioperative Outcomes Group", Anesth Analg, Mar. 1997, 84(3), 578-84.
Horlocker et al, "Neurologic complications of 603 consecutive continuous spinal anesthetics using macrofiber optic probe and microfiber optic probe techniques", Perioperative Outcomes Group. Anesth. Analg., Jan. 10, 1997, 84(5),1063-70.
Horlocker et al, "Small Risk of Serious Neurologic Complications Related to Lumbar Epidural Fiber Optic Probe Placement in Anesthetized Patients", Anesth. Analg., 2003, 96(6), 1547-1552.
International Patent Application No. PCT/US2012/069626: International Search Report and the Written Opinion dated Feb. 20, 2013, 17 pages.
Jakeman, E., "Photo Correlation, in Photon Correlation and Light Beating Spectroscopy", H.Z. Cummins and E.R. Pike, Editors. 1974, Plenum: New York: p. 75-149.
Jia et al, "Critical Care of Traumatic Spinal Cord Injury", J. Intensive Care Med., 2011.
Jones et al, "Medical Surveillance of Injuries in the U.S. Military Descriptive Epidemiology and Recommendations for Improvement", Am. J. Prev. Med., Jan. 2010, 38(1 Suppl), S42-60.
Kaplan et al, "Effects of Aortic Occlusion on Regional Spinal Cord Blood Flow and Somatosensory Evoked Potentials in Sheep", Neurosurgery, 1987. 21(5), 668-75.
Kattail et al, "Epidemiology and Clinical Outcomes of Acute Spine Trauma and Spinal Cord Injury: Experience From a Specialized Spine Trauma Center in Canada in Comparison With a Large National Registry", J. Trauma, Nov. 2009, 67(5), 936-43.
Kim et al, "Noninvasive Measurement of Cerebral Blood Flow and Blood Oxygenation Using Near-Infrared and Diffuse Correlation Spectroscopies in Critically Brain-Injured Adults", Neurocrit Care, Apr. 2010, 12(2),173-80.
Knapik et al, "A Systematic Review of Post-Deployment Injury-Related Mortality Among Military Personnel Deployed to Conflict Zones", BMC Public Health, Jul. 13, 2009. 9, 231.
Krahl et al, "Systematic Review of Military Motor Vehicle Crash-Related Injuries", Am. J. Prev. Med., 2010, 38(1 Suppl), S189-96.
Krause, J.S. and J.L. Coker, "Aging After Spinal Cord Injury: A 30-year Longitudinal Study", J. Spinal Cord. Med., 2006, 29(4), 371-376.
Krull et al, Motor Vehicle Fatalities Among Men in the U.S. Army from 1980 to 1997. Mil. Med., Nov. 2004, 169(11), 926-31.

Lehr et al, "An Intra-Aortic Shunt Prevents Paralysis During Aortic Surgery in Sheep", J. Surg. Res., Jul. 2007, 141(1), 78-82.
Lesser et al, "Postoperative Neurological Deficits May Occur Despite Unchanged Intraoperative Somatosensory Evoked Potentials", Ann. Neurol., 1986, 19(1), 22-5.
Lewis, "Spinal Injuries Caused by the Acceleration of Ejection", J R Army Med Corps, 2002, 148(1), 22-26.
Lin et al, "Anesthesia in Sheep With Propofol or With Xylazine-Ketamine Followed by Halothane", Vet. Surg., 1997, 26(3), 247-52.
Luchtel et al, "Histological Methods to Determine Blood Flow Distribution With Fluorescent Microspheres", Biotech Histochem, 1998, 73(6), 291-309.
Macgregor et al, "Injuries Sustained in Noncombat Motor Vehicle Accidents During Operation Iraqi Freedom" Injury, Sep. 2012, 43(9), 1551-1555.
Mackenzie, R., "Spinal injuries", J R Army Med Corps, 2002, 148(2),163-71.
Mahmoud et al, "Susceptibility of Transcranial Electric Motor-Evoked Potentials to Varying Targeted Blood Levels of Dexmedetomidine During Spine Surgery", Anesthesiology, Jun. 2010, 112(6), 1364-1373.
McCarthy et al, "Neurologic outcomes with cerebral oxygen monitoring in traumatic brain injury", Surgery, Jun. 18, 2009, 146(4), 585-90; discussion 590-1.
Mesquite, R.C. and A.G. Yodh, "Diffuse Optics: Fundamentals and Tissue Applications", In Proceedings of the International School of Physics "Enrico Fermi" Course CLXXIII, Kaiser R., D.S. Weirsma, L. Faillini, eds. IOP Press: Amsterdam, 2011, 51-74.
Modi et al, "False-negative transcranial motor-evoked potentials during scoliosis surgery causing paralysis: a case report with literature review", Spine (Phila Pa 1976), Nov. 15, 2009, 34(24), p. E896-900.
Moomiaie et al, "Elefteriades, Cooling fiber optic probe for spinal cord preservation in thoracic aortic surgery", J. Cardiovasc. Surg. (Torino), 2007, 48(1),103-8.
Narotam et al, "Brain Tissue Oxygen Monitoring in Traumatic Brain Injury and Major Trauma: Outcome Analysis of a Brain Tissue Oxygen-Directed Therapy", J. Neurosurg., Oct. 2009, 111(4), 672-682.
Oyinbo, C.A., "Secondary Injury Mechanisms in Traumatic Spinal Cord Injury: A Nugget of This Multiply Cascade", Acta Neurobiol Exp (Wars), 2011, 71(2), 281-99.
Pastorelli et al, "The Prevention of Neural Complications in the Surgical Treatment of Scoliosis: The Role of the Neurophysiological Intraoperative Monitoring", Eur. Spine J., 2011, 20 Suppl 1, S105-14.
Patil et al, "Complications and outcomes after spinal cord tumor resection in the United States from 1993 to 2002", Spinal Cord, 2008, 46(5), 375-379, Published Online: Dec. 11, 2007.
Peleg, K. and D.H. Jaffe, "Are injuries from terror and war similar? A comparison study of civilians and soldiers", Ann. Surg., Aug. 2010, 252(2), 363-9.
Pflaum et al, "Worklife after traumatic spinal cord injury", J. Spinal Cord. Med., 2006, 29(4), 377-86.
Pirouzmand, F., "Epidemiological Trends of Spine and Spinal Cord Injuries in the Largest Canadian Adult Trauma Center From 1986 to 2006", J. Neurosurg. Spine., Feb. 2010, 12(2),131-40.
Ragel et al, "Fractures of the Thoracolumbar Spine Sustained by Soldiers in Vehicles Attacked by Improvised Explosive Devices", Spine, Oct. 15, 2009, 34(22), 2400-2405.
Reames et al, "Complications in the Surgical Treatment of 19,360 Cases of Pediatric Scoliosis: A Review of the Scoliosis Research Society Morbidity and Mortality Database", Spine, Aug. 15, 2011, 36(18),1484-1491.
Roche-Labarbe et al, "Noninvasive Optical Measures of CBV, StO(2), CBF index, and rCMRO(2) in Human Premature Neonates' Brains in the First Six Weeks of Life", Hum. Brain Mapp, Mar. 2010, 31(3), 341-52.
Rose et al, "Epidural, Intrathecal Pharmacokinetics, and Intrathecal Bioavailability of Ropivacaine", Anesth. Analg, Sep. 2007, 105(3), 859-67.

(56) References Cited

OTHER PUBLICATIONS

Schoenfeld et al, "Incidence and Epidemiology of Spinal Cord Injury Within a Closed American Population: The United States Military (2000-2009)", Spinal Cord, Mar. 2011, 49(8), 874-879.
Scoville et al, "Traumatic Deaths During U.S. Armed Forces Basic Training, 1977-2001", Am. J. Prev. Med., Apr. 2004, 26(3), 194-204.
Senier et al, "Hospitalizations for Fall-Related Injuries Among Active-Duty Army Soldiers", 1980-1998 Work, 2002, 18(2),161-70.
Shang et al, "Effects of Muscle Fiber Motion on Diffuse Correlation Spectroscopy Blood Flow Measurements During Exercise", Biomed. Opt Express, Aug. 5, 2010, 1(2), 500-511.
Simonovich et al, "Real-Time Monitoring of Mitochondrial NADH and Microcirculatory Blood Flow in the Spinal Cord", Spine, Nov. 1, 2008, 33(23), 2495-502.
Sloan et al, Multimodality Monitoring of the Central Nervous System Using Motor-Evoked Potentials. Curr. Opin. Anaesthesiol, Oct. 2008, 21(5), 560-4.
Smith et al, "Health-related quality of life for veterans with spinal cord injury", Spinal Cord, Feb. 2008, 46(7), 507-12.
Strauss et al, "Trends in Life Expectancy After Spinal Cord Injury", Arch. Phys. Med. Rehabil., Aug. 2006, 87(8), 1079-85.
Sunar et al, "Noninvasive Diffuse Optical Measurement of Blood Flow and Blood Oxygenation for Monitoring Radiation Therapy in Patients With Head and Neck Tumors: A Pilot Study", J. Biomed. Opt., Nov./Dec. 2006, 11(6), 064021.
Svensson et al, "Spinal Cord Anatomy of the Baboon—Comparison With Man and Implications for Spinal Cord Blood Flow During Thoracic Aortic Cross-Clamping", S. Afr. J. Surg., Mar. 1986, 24(1), 32-4.
Swenson et al, "The Effect of Prior Dural Puncture on Cerebrospinal Fluid Sufentanil Concentrations in Sheep After the Administration of Epidural Sufentanil", Anesth. Analg., r Apr. 1998, 86(4), 794-6.
Szelenyi et al, "Transcranial electric stimulation for intraoperative motor evoked potential monitoring: Stimulation parameters and electrode montages", Clin. Neurophysiol., Jul. 2007, 118(7),1586-95.
Thuret et al, "Therapeutic Interventions After Spinal Cord Injury", Nat. Rev. Neurosci., Aug. 2006, 7(8), 628-43.
Turnbull, I.M., "Chapter 5., Blood Supply of the Spinal Cord: Normal and Pathological Considerations", Clin. Neurosurg., 1973. 20, 56-84.
Van den Berg et al, "Incidence of spinal cord injury worldwide: a systematic review", Neuroepidemiology, Feb. 2010, 34(3),184-92; discussion 192.
Van Oosterhout et al, "Fluorescent Microspheres to Measure Organ Perfusion: Validation of a Simplified Sample Processing Technique", Am J Physiol, Aug. 1, 1995. 269(2 Pt 2), H725-33.
Vialle et al, "The Feasibility of Detecting Motor and Sensory Potentials in a Sheep Model", Lab. Anim., Oct. 1, 2006, 40(4), 469-73.
Wang et al, "Impact of Anesthesia on Transcranial Electric Motor Evoked Potential Monitoring During Spine Surgery: A Review of the Literature". Neurosurg Focus, Oct. 2009, 27(4), E7.
Werner, U., "Ejection Associated Injuries Within the German Air Force from 1981-1997. Aviat Space", Environ Med, Dec. 1999, 70(12), 1230-4.
Hammell, K. "Quality of Life After Spinal Cord Injury: A Meta-Synthesis of Qualitative Findings", Spinal Cord, 2007, 45(2),124-39, Published Online Nov. 7, 2006.
Wheatley et al, "Safety and Efficacy of Postoperative Epidural Analgesia", Br. J. Anaesth., 2001, 87(1), 47-61.
Wilson, J.R. and M.G. Fehlings, "Emerging Approaches to the Surgical Management of Acute Traumatic Spinal Cord Injury", Neurotherapeutics, Apr. 2011, 8(2),187-94.
Wolbeek et al, "Value and Pitfalls of Neurophysiological Monitoring in Thoracic and Thoracoabdominal Aortic Replacement and Endovascular Repair", Thorac. Cardiovasc. Surg., 2010, 58(5), 260-4.
Wyndaele, M. and J.J. Wyndaele, "Incidence, Prevalence and Epidemiology of Spinal Cord Injury: What Learns a Worldwide Literature Survey?" Spinal Cord, Jan. 2006, 44(9), 523-9.
Wynn et al, "Complications of Spinal Fluid Drainage in Thoracoabdominal Aortic Aneurysm Repair: A Report of 486 Patients Treated From 1987 to 2008", J. Vasc. Surg., Jan. 2009. 49(1), 29-34; discussion 34-5.
Yodh, A. and B. Chance, "Spectroscopy and Imaging With Diffusing Light", Phys. Today, Mar. 1995, 48, 34-40.
Yu et a, "Real-time In Situ Monitoring of Human Prostate Photodynamic Therapy With Diffuse Light", Photochem Photobiol, May 2006, 82(5), 1279-84.
Yu et al, "Time-Dependent Blood Flow and Oxygenation in Human Skeletal Muscles Measured With Noninvasive Near-Infrared Diffuse Optical Spectroscopies", J. Biomed. Opt, Mar./Apr. 2005, 10(2), 024027.
Yu et al, "Validation of Diffuse Correlation Spectroscopy for Muscle Blood Flow With Concurrent Arterial Spin Labeled Perfusion MRI". Opt Express, Feb. 5, 2007, 15(3),1064-75.
Yu et al, "Major Medical Conditions and Va Healthcare Costs Near End of Life for Veterans With Spinal Cord Injuries and Disorders", J. Rehabil. Res. Dev., 2008, 45(6), 831-840.
Zeilig et al, "Civilian Spinal Cord Injuries Due to Terror Explosions", Spinal Cord, 2010, 48(11), 814-818, Publsihed Online: Mar. 23, 2010.
Radhakrishnan et al, "Light Scattering From Rat Nervous System Measured Intraoperatively by Near-Infrared Reflectance Spectroscopy", Journal of Biomedical Optics, 10(5), Sep./Oct. 2005, 0514051-1-0514051-8.
Macnab et al, "Infrared Spectroscopy for Intraoperative Monitoring of the Spinal Cord" Spine, 27(1), Jan. 1, 2002, 17-20.
European Patent No. 12857335.9: Supplementary European Search Report dated Jun. 24, 2015, 4 pages.

* cited by examiner

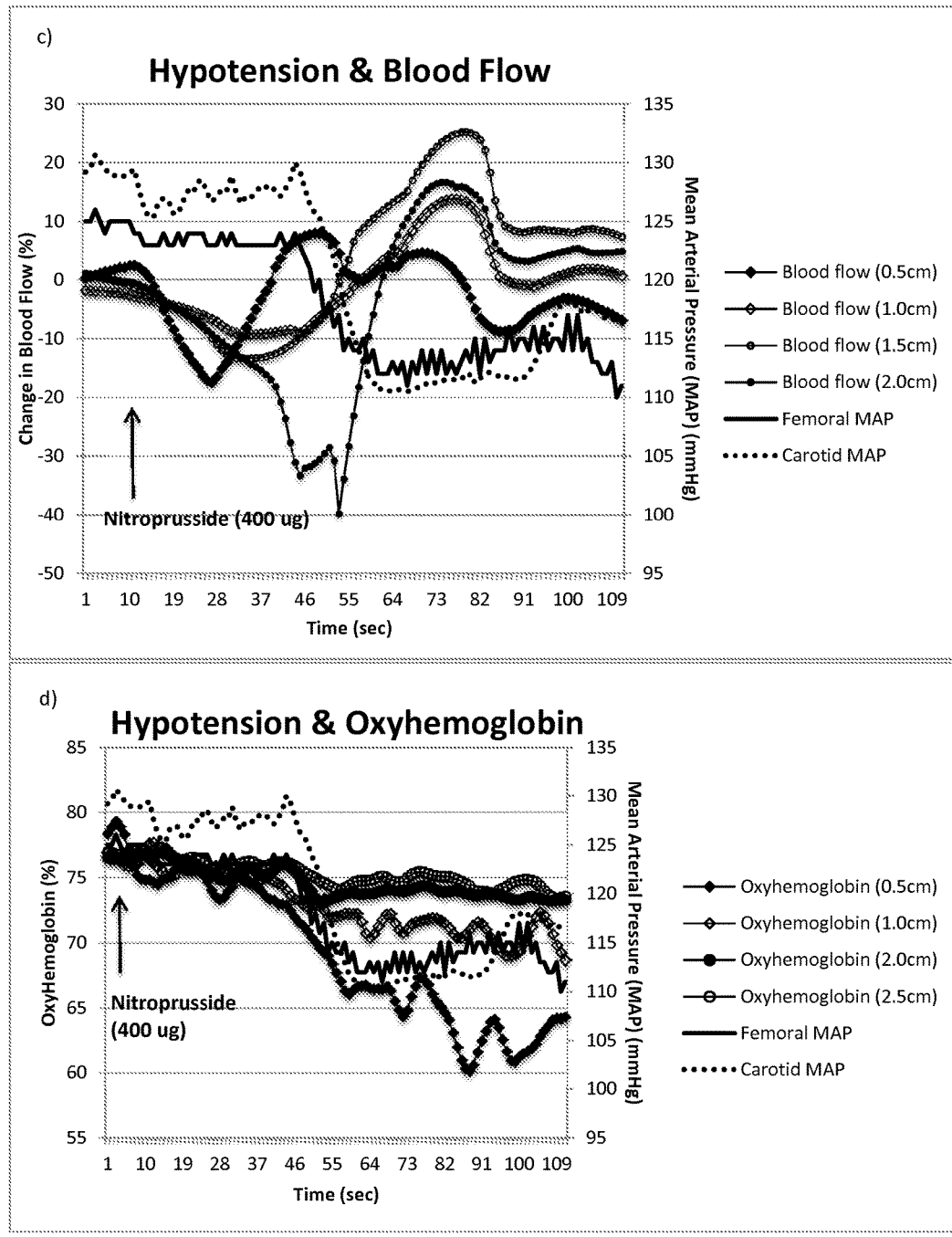
Figure 2c-d

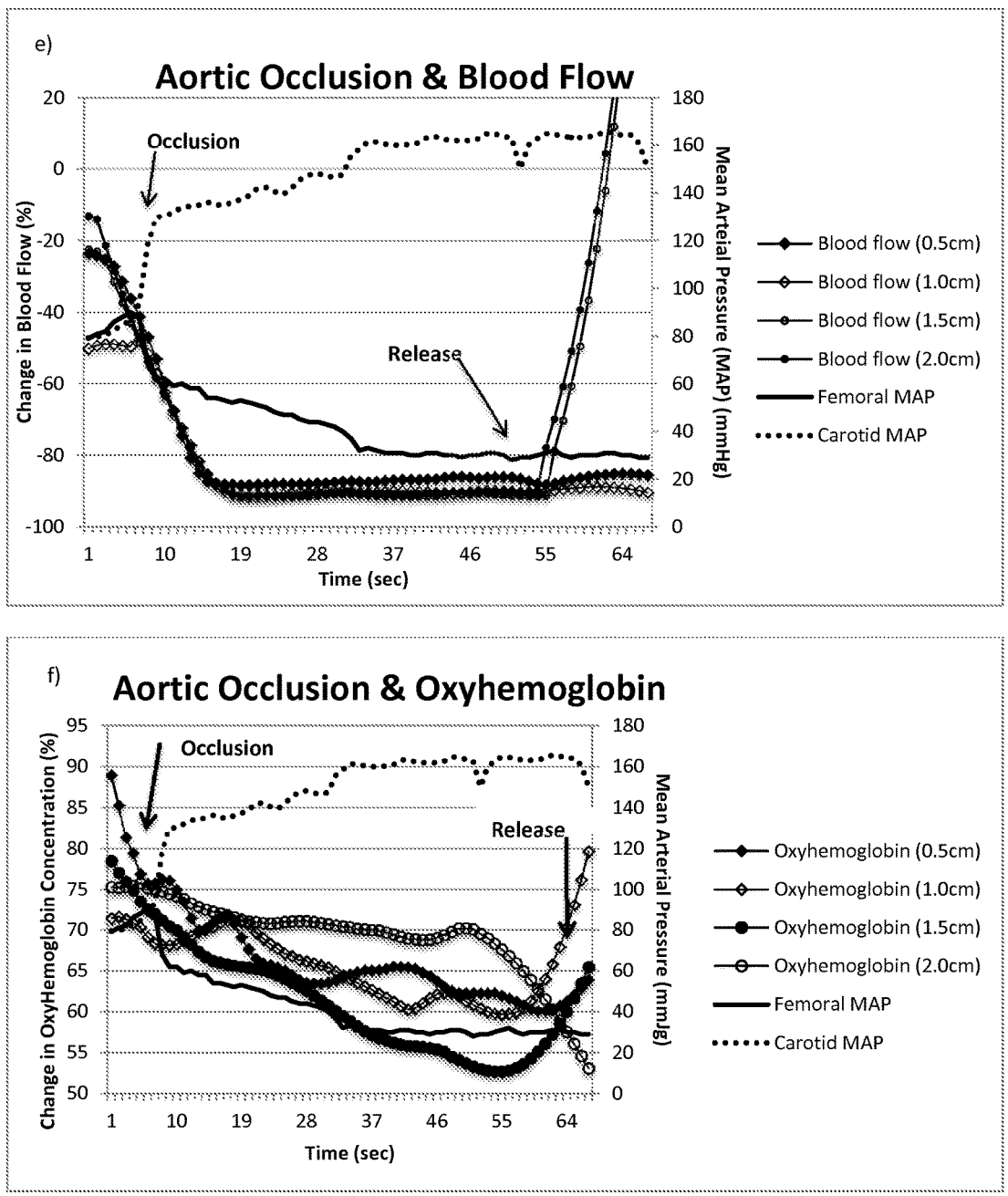
Figure 2e-f

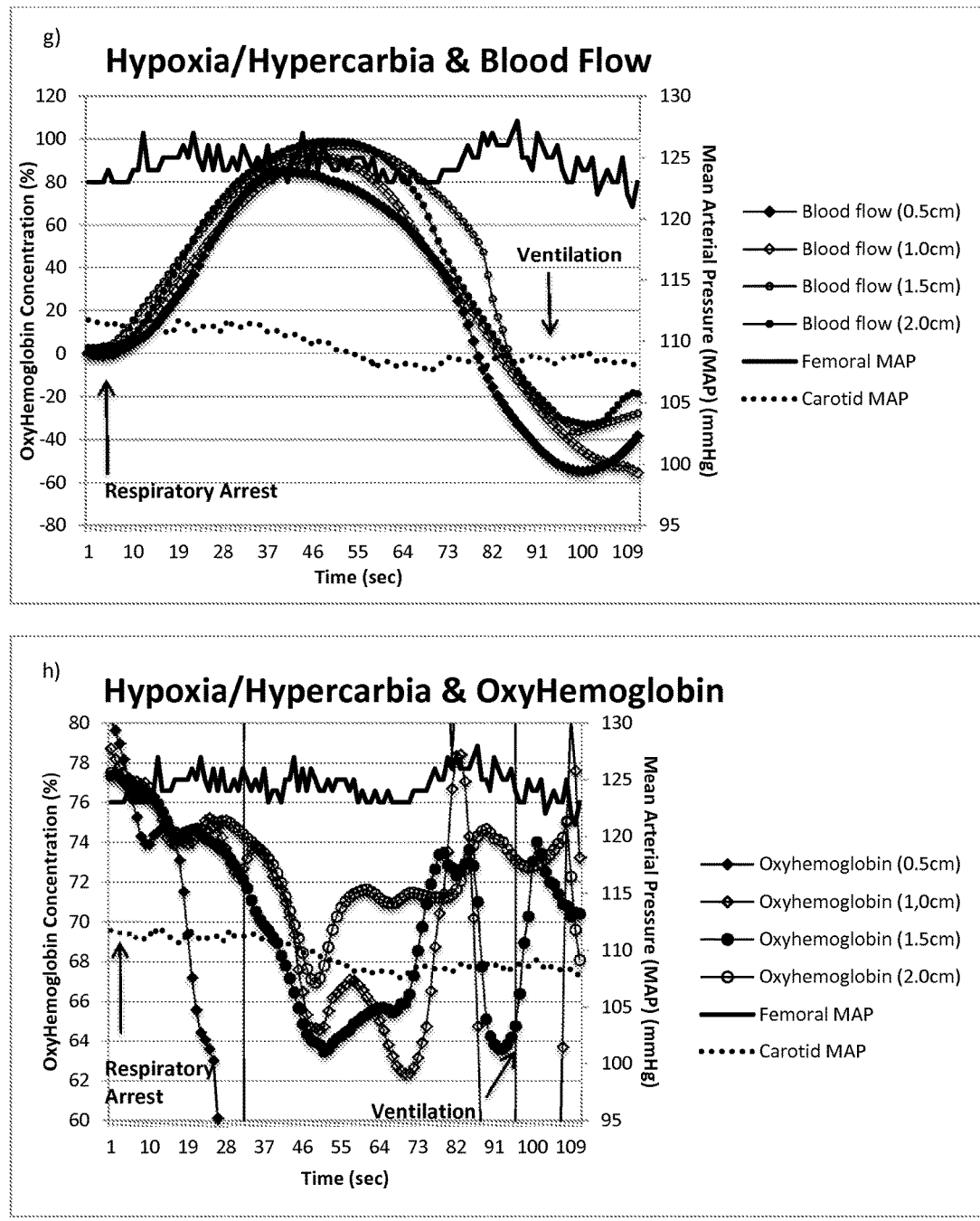
Figure 2g-h

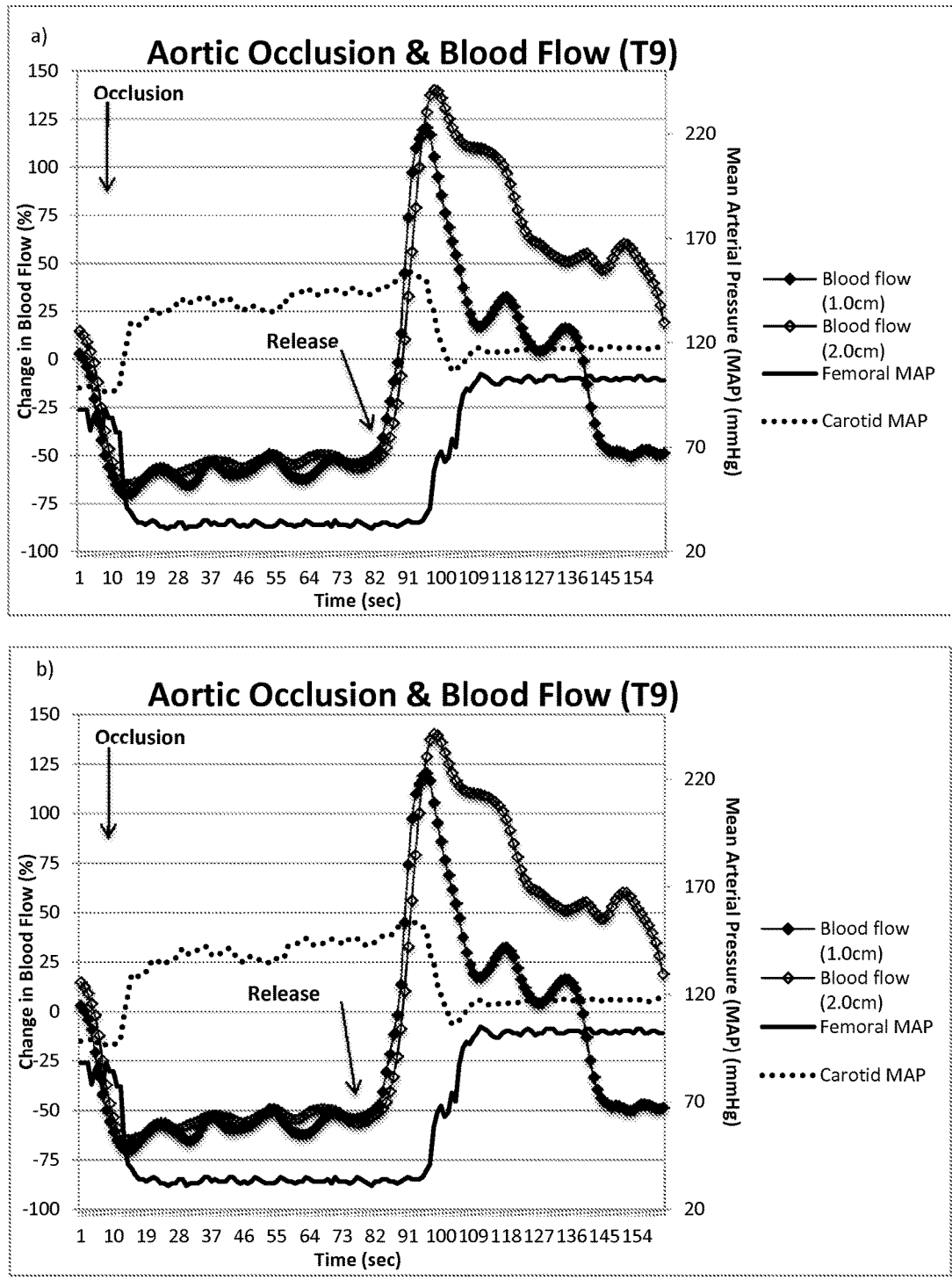
Figure 3a-b

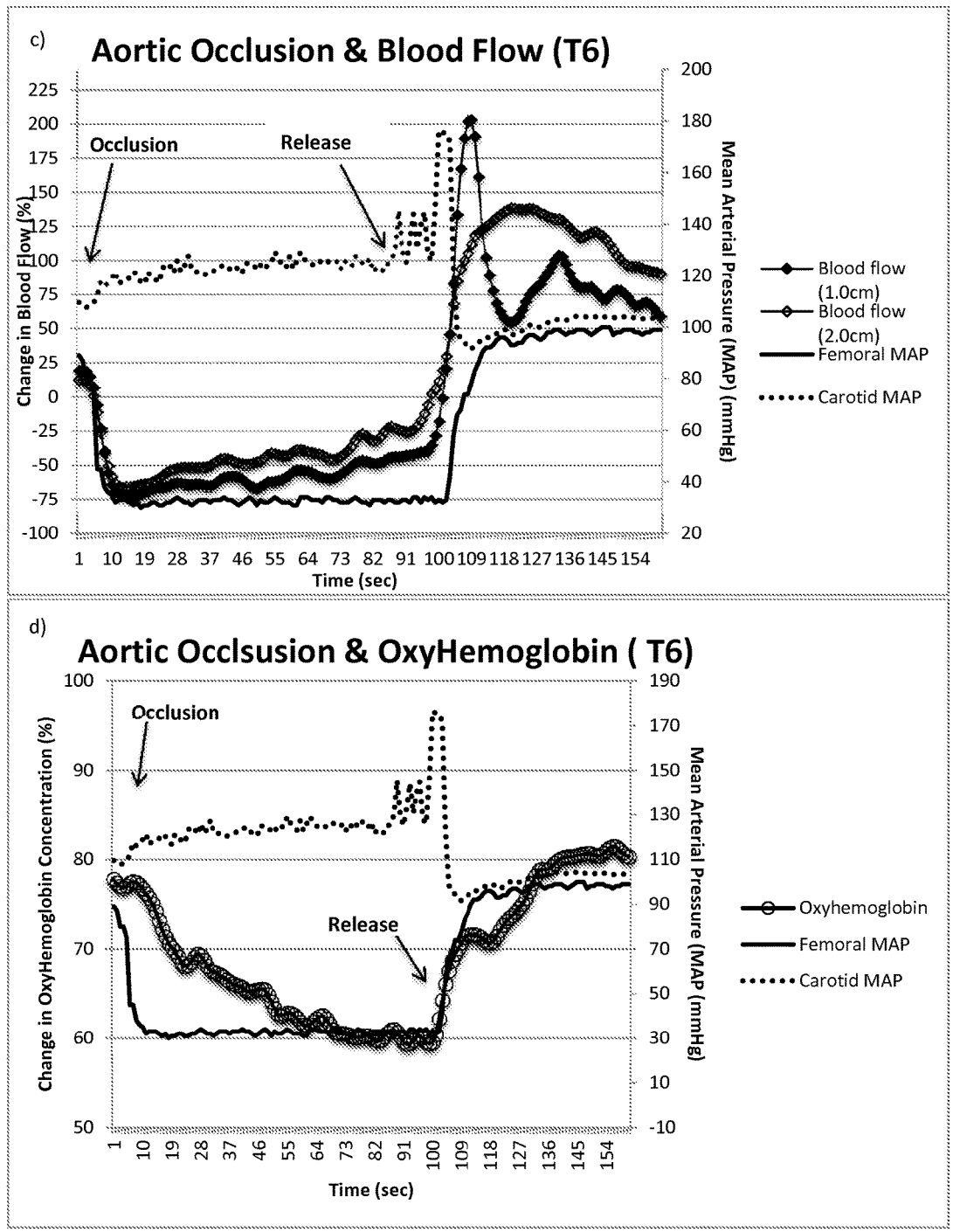
Figure 3c-d

FIBER OPTIC FLOW AND OXYGENATION MONITORING USING DIFFUSE CORRELATION AND REFLECTANCE

CROSS-REFERENCE TO RELATED APPLICATIONS

This application is the National Stage of International Application No. PCT/US2012/069626, filed Dec. 14, 2012, which claims the benefit of and priority to U.S. Provisional Application No. 61/570,349, filed Dec. 14, 2011, the entireties of which applications are incorporated herein by reference for any and all purposes.

TECHNICAL FIELD

The present disclosure relates to the field of spectroscopic instruments, to the field of tissue assessment, and to the fields of spine and spinal cord surgery and spinal cord injury.

BACKGROUND

Spinal cord ischemia resulting in paralysis and paresis may occur after trauma, during surgical correction of spine deformities, during major vascular surgery, following pain management procedures, and may also occur as a result of vascular disorders. Hypotension, hypoxia, vasospasm, inflammation, edema, and hemorrhage all propagate spinal ischemia after injury. Prevention of secondary injury from ischemia may limit disability. Preventing secondary injury to the spinal cord, as with the brain, requires continued hemodynamic support and often, early surgical intervention. Prevention of secondary spinal injury is focused upon the preservation or restoration of spinal cord blood flow and oxygen delivery. No existing method, however, is available for measuring or monitoring the impact of interventions upon these critical parameters.

In the cases of cerebral ischemia and traumatic brain injury, improvement in outcome has come from an improved ability to monitor, in real time, the success of interventions such as angioplasty, thrombolysis, intracranial pressure, and cerebral oxygenation. Efforts focused upon ameliorating spinal cord injury have thus far met with dismal results.

Currently, the only methods employed for assessment of spinal cord ischemia are based on electrophysiology, including both somatosensory (SSEP) and motor (MEP) evoked potentials. These technologies monitor the integrity of posterior spinal somatosensory and anterior/lateral spinal motor tracts, respectively; when combined, they can identify injury, offer insight into the impact of particular interventions, and thereby provide an opportunity to limit or reverse injury. Such neuro-electrophysiological monitoring, however, may be not infrequently influenced by anesthetic management, patient temperature, limb ischemia and technological malfunctions (lead displacement, disconnection, etc.). Furthermore, accurate and timely interpretation of these data requires skilled neurologists with expertise in neuro-electrophysiological monitoring. "False negatives", wherein patients have awakened with serious deficits in spite of "normal" evoked potentials, and "false positives", wherein patients have awakened without deficits in spite of loss or degradation of signal, have both been reported by SSEP and MEP monitoring. Finally, abnormalities in neuro-electrophysiological measurements may be delayed relative to the inciting event, which diminishes chances for rescue of threatened tissues. Despite these limitations, MEP and SSEP remain the "gold standard" for functional monitoring of the spinal cord during aortic, spine, and spinal cord surgery.

Tools available to measure spinal cord blood flow are extremely limited. The ability to measure spinal cord blood flow with laser Doppler has been demonstrated in both animal and human studies. These devices, however, measure flow in a very limited tissue volume, in close proximity to the probe tip. LDF sampling volumes are estimated at 0.3-0.5 mm$^3$. Additionally, positioning of the rigid probe is troublesome, the probes are prone to fracture, and they cannot be left in place for an extended period of time. Noninvasive methods for spinal cord blood flow measurement have been superficially investigated; they include single photon emission computed tomography and MRI based arterial spin labeling. MRI and CT may become excellent tools for the measurement of spinal cord blood flow and can even be expected to have superior spatial sensitivity. Intraoperative monitoring with both MRI and CT, however, is simply not feasible and these tools certainly would not allow for continuous monitoring. Indeed, no current approach can be reasonably applied in a field surgical hospital.

The ability to measure spinal cord blood flow and oxygenation would: 1) aid in the ability to expeditiously diagnose and monitor the progress of spinal cord ischemia; 2) offer an enhanced opportunity to prevent secondary injury; 3) allow the assessment of the efficacy of interventions aimed at ameliorating ischemia; 4) assist in early surgical stabilization of spinal trauma; 5) allow for the continuous assessment of spinal cord blood flow and oxygenation for several days after surgery; and 6) assist in the laboratory and clinical assessment of the efficacy of novel therapeutic approaches to ameliorate ischemia. Finally, the ability to combine MEP/SSEP with blood flow/oxygenation monitoring would provide key additional insight into the mechanism of injury. Accordingly, there are needs in the art for devices capable of measuring spinal cord blood flow and or oxygenation and also for related methods.

SUMMARY

To meet the monitoring needs described above, disclosed are fiber optic devices and related methods that allow for, inter alia, measurement of spinal cord flow and oxygenation. Such devices may have broad applicability, in the management of acute spinal cord trauma, in the intraoperative and postoperative management of patients undergoing surgery upon the spine or spinal cord, or major vascular surgery where the blood supply to the spinal cord may be compromised. The devices may enhance the efficacy of interventions aimed at the prevention of primary and secondary ischemic injury, and ultimately improving neurologic outcome.

The present disclosure first provides devices. These devices suitably include a first illuminator fiber having a distal end; and a first detector fiber having a distal end located at a first distance from the distal end of the first illuminator fiber, the first illuminator fiber being in optical communication with an illumination source, and the first detector fiber being capable of optical communication with a first illumination detector.

Also provided are methods, including illuminating, with light emitted from the distal end of an illuminator fiber, a first region of tissue proximate to the spinal cord; collecting, with a first detector fiber having a distal end at a distance from the distal end of the illuminator fiber, illumination from the first region of tissue; and correlating the collected illumination to a level of tissue blood oxygenation, a level of tissue oxy-hemoglobin, a level of tissue deoxy-hemoglobin, a level of tissue blood flow, water content, lipid presence, exogenous tracer presence, or any combination thereof.

Additionally provided are devices, the devices including an elongated fiber optic probe being adapted for insertion into the epidural space, the intrathecal space, or both; the with a first illuminator fiber having a distal end being integrated; a first detector fiber being integrated with the fiber optic probe, the first detector fiber having a distal end located at a first distance from the distal end of the first illuminator fiber, the first illuminator fiber being capable of optical communication with an illumination source, the first detector fiber being capable of optical communication with a first illumination detector.

Further provided are methods, the methods including illuminating, with light emitted from the distal end of an illuminator fiber integrated with a fiber optic probe, a first region of tissue proximate to the spinal cord; collecting, with a first detector fiber integrated with the fiber optic probe and having a distal end at a distance from the distal end of the illuminator fiber, illumination from the first region of tissue; and correlating the collected illumination to a level of tissue blood oxygenation, a level of tissue oxy-hemoglobin, a level of tissue de-oxy-hemoglobin, a level of tissue blood flow, water content, lipid presence, exogenous tracer presence, or any combination thereof.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale or proportion. In the drawings:

FIG. 3(a-d) depicts the results from the linearly arrayed, clinical fiber optic device, with a single source and two detectors, as is depicted in FIG. 1, placed into the epidural space. Spinal cord blood flow and oxygenation responses to intra-aortic balloon occlusion are displayed from levels L-1 and T-9.

DETAILED DESCRIPTION OF ILLUSTRATIVE EMBODIMENTS

Figure 1:
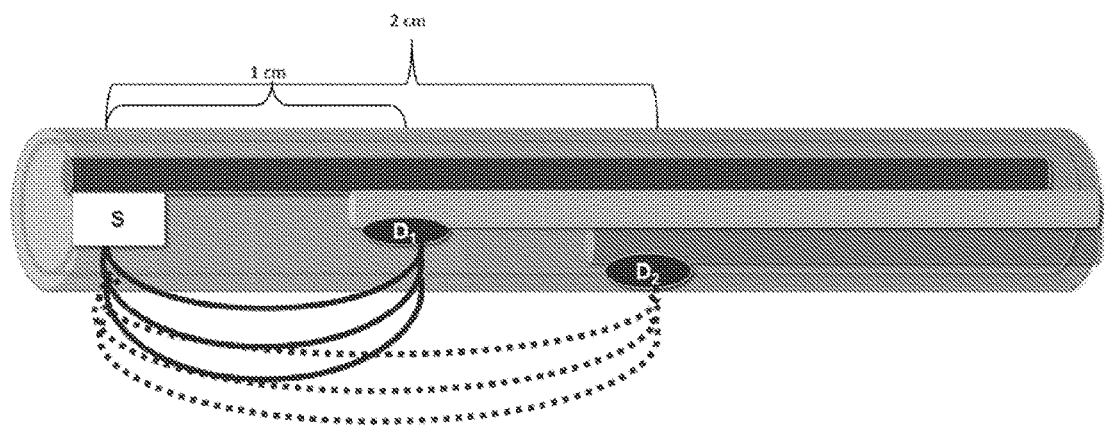
FIG. 1 illustrates an exemplary probe that uses a single illuminator source fiber and two detector fibers. The source fiber is shared for both diffuse correlation spectroscopy (DCS) and diffuse optical spectroscopy (DOS) through an optical switch. Each detector location has a pair of single mode and multimode fibers. The single mode fibers are used to detect the blood flow, as monitored by DCS, while the multimode fibers detect the blood oxygenation measured using DOS. This probe is flexible and thin (less than 1 mm thick), and is about 3 m long, which permits flexibility in accommodating the instrument in the operating room or intensive care unit. The source-detector separations can vary from, e.g., about 0.5 cm to about 2.0 cm or even about 5 cm in some embodiments, which in turn allows interrogation to depths of approximately 0.0 cm to about 1.0 cm or even about 2 cm. In the FIG. 1 depiction, the probe is located upon the posterior spinal cord, with the source positioned closer to the head and the two detectors inferiorly. The solid and dashed lines depict most probable path lengths of light between the source and detectors. Greater separation between the source and the detector may yield interrogation of deeper spinal cord depths. The photo represents the fiber optic probe positioned under the dura after laminectomy.

The present disclosure may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality," as used herein, means more than one. When a range of values is expressed, another embodiment includes from the one particular value and/or to the other particular value. Similarly, when values are expressed as approximations, by use of the antecedent "approximately" or "about," it will be understood that the particular value forms another embodiment. All ranges are inclusive and combinable, and any documents cited herein are incorporated by reference in their entireties for any and all purposes.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any sub-combination. Further, references to values stated in ranges include each and every value within that range.

In a first aspect, the present disclosure provides devices. These devices suitably include a first illuminator fiber having a distal end; and a first detector fiber having a distal end located at a first distance from the distal end of the first illuminator fiber, the first illuminator fiber being in optical communication with an illumination source, and the first detector fiber also being capable of being in optical communication with a first illumination detector.

Devices may include a computer processor in communication with the first illumination detector. The computer processor is suitably adapted to estimate, based on illumination received by the first illumination detector, blood oxygenation, oxy-hemoglobin, deoxy-hemoglobin, blood flow, oxygen metabolism, water presence or concentration, lipid presence or concentration, exogenous tracer presence, or any combination thereof. A tracer may be an agent such as a labeled antibody or other species that is complementary to a particular cell or molecule. For example, the agent may be an antibody or other labeled protein that binds to cancerous cells. The tracer may also be a dye or fluorophore, such as a fluorescent dye, a calcium-sensitive or pH-sensitive dye. In this way, the device may be used to assess the presence of the tracer in tissue proximate to the spinal cord or otherwise proximate to the device. The tracer may have a fluorescent component, and may fluoresce under illumination applied by the illuminator fiber or other source. The term "proximate" should be understood to mean that bodies proximate to one another may touch one another, or may be within up to about 10 cm or even 20 cm from one another.

The disclosed devices may, in some embodiments, include a second and/or additional detector fibers. The second detector fiber suitably has a distal end that is located at a second distance from the distal end of the first illuminator fiber. The distance between the distal end of the first illuminator and the distal end of the first detector fiber may be from 0.01 mm to about 20 cm, or from 0.1 mm to about 10 cm, or from 1 mm to about 1 cm. Distances of between 0.1 and 2 cm are especially suitable, but are not mandatory. The source and detector fiber positions can also be exchanged and still provide the same results.

The distance between the distal end of first illuminator and the distal end of the second detector fiber may, similarly, be from about 0.01 mm to about 20 cm, or from about 0.1 mm to about 10 cm, or from 1 mm to about 1 cm. Distances of between about 0.1 and about 2.0 cm are especially suitable, but are not required. The distance between the distal ends of the illuminator fiber and the first detector fiber suitably differs from the distance between the distal ends of the illuminator fiber and the second detector fiber. This allows for the user to interrogate tissues at two or more different distances (which may be thought of as depths) from the illuminator fiber at the same time, as described in U.S. application Ser. No. 11/106,390, "Optical Measurement Of Tissue Blood Flow, Hemodynamics And Oxygenation" (filed Apr. 13, 2005), incorporated herein by reference.

The second detector fiber is suitably in optical communication with the first illumination detector, although the fiber may be in optical communication with a second illumination detector. The device may be configured such that the illuminator fiber provides illumination of one or more wavelengths. For example, the illuminator fiber may be configured such that it alternates between providing illumination of first and second wavelengths. The detector may in turn be configured to detect illumination collected by the first and second detector fibers at different wavelengths.

In one exemplary embodiment, a device may be constructed to assess blood oxygenation and also blood flow. For detection of oxygenation, one may use a multimode fiber. Fibers from OZ optics, Thorlabs, and Fiber Optic Systems are all considered suitable. The fiber may be of a length suited to the user's needs; in exemplary embodiments, the fiber may be from 5 to 10 meters in length, which length allows a user to insert the fiber into the epidural or intrathecal space and to have sufficient slack to enable advancement within the space, and ease of monitoring from a distance. The diameter of the fiber is suitably in the range of from about 1, 2, or 10 microns to about 1 mm or even 3 mm; diameters in the range of between about 200 microns to about 1 mm; 500 micron diameter fibers are considered suitable. The illumination wavelength for oxygenation analysis is suitably in the near-IR range, i.e., in the range of from about 600 nm to about 970 nm. One may apply two or more wavelengths to a sample; wavelengths of 690, 785, or 830 nm are also considered suitable for oxygenation analysis.

For blood flow analysis, one may use a single-mode fiber. Such fibers are commercially available from the suppliers listed above. The single-mode fibers are suitably of the lengths described; the diameter of the single-mode fibers may be smaller than the diameter of the multimode fibers. Single mode fibers may, for example, have a diameter in the range of from about 1 or even about 3 microns to about 100 microns, or even 2 microns to about 50 microns. A long-coherent laser may be used; lasers with about 20 m of coherence length may be used. The wavelengths for blood flow assessment may be in the near-IR range, such as wavelengths of about 785, 690, or 830 nm. Water concentration may be assessed by illumination in the range of about 850 nm or even above about 850 nm.

A user may also measure cytochrome concentration, or even lipid concentration. A user may also apply the disclosed devices to assess perfusion of flow into tissue. One way of doing so is to administer indocyanine (ICG) dye to a patient. ICG dye may be better-retained by cancerous tissue, so a user may assess a tissue region for the presence of ICG; by comparing the ICG uptake of that region, the user may determine whether the region under study may be cancerous in nature.

Fibers may be bundled together. The fibers may be held together with ties or other reinforcements. The fibers may also be bonded together. Fibers are suitably disposed within a housing (also referred to as a "casing") or jacket, as described elsewhere herein. Such jackets are suitably adapted for insertion or implantation into a subject; polyethylene and other polymers and copolymers are considered suitable housing materials. The housing may have a diameter of about 1, 2, 5, or 10 mm, although other diameters may be used, depending on the user's needs.

Illumination detectors may be various devices. In one embodiment, the detector is a photodiode, or even an avalanche photodiode. The detector may also be a photomultiplier tube, a CCD camera, and the like. The devices may include two or more detector devices. The device may have different illumination detectors connected to different fibers. For example, the first detector fiber may be in optical communication with a first detection device (e.g., a CCD), and a second detector device in optical communication with a second detection device (e.g., a photodiode). By detecting the presence of different wavelengths of illumination collected by the detector fibers, the user may assay for two or more characteristics. For example, By employing two or more detection fibers having distal ends at different distances from the distal end, the device may assay regions at multiple distances from the device, offering depth or spatial resolution, and or discrimination of differences in flow, oxygenation, or other characteristics between the anterior and posterior spinal cord vascular beds. This in turn enables the user to collect more complete information concerning the condition of the subject. For example, the user may determine that oxygenation is within a normal range 1 cm away from a device placed in the epidural space, but that oxygenation is below a normal range 2 cm away from the device. The user may then make the necessary adjustment (e.g., checking a surgical site, manipulating an instrument) so as to achieve normal blood flow 2 cm away from the device. The devices may be configured to collect information in real or near-real time. This real-time information in turn empowers the user to make appropriate adjustments or interventions needed to return the subject to normal conditions. The devices may, in some embodiments, include a third detector fiber having a distal end at a third distance from the distal end of the first illuminator fiber. This in turn allows the user to investigate conditions in tissue at a third distance from the device. As one example, a device with three detector fibers having distal ends at three distances from the distal end of the illuminator fiber may provide information concerning tissue at about 1, 3, and 5 cm from the illuminator fiber. The use of more detector fibers can also allow tomographic reconstructions of oxygenation and flow below the optical probe.

In other embodiments, the devices may include a second or multiple illuminator fibers. The second illuminator fiber may have a distal end that terminates at a distance from the distal end of the first illuminator fiber. Such devices may include individual detector fibers that are associated with each of the illuminator fibers. For example, a device may include a first illuminator fiber having a distal end that terminates—when the device is inserted—at thoracic region of the spine. First and second detector fibers may in turn have distal ends that terminate, respectively, about 1 and 2 cm from the distal end of the first illuminator fiber. The second illuminator fiber may have a distal end that terminates at the lumbar region, and third and fourth detector fibers may have distal ends that terminate, respectively, about 1 and 2 cm from the distal end of the second illuminator fiber. The second illuminator fiber may supply illumination that is the same (in terms of wavelength) as the first illuminator fiber. Alternatively, the second illuminator fiber may provide illumination that differs in wavelength from illumination supplied by the first illuminator fiber.

Figure 8:
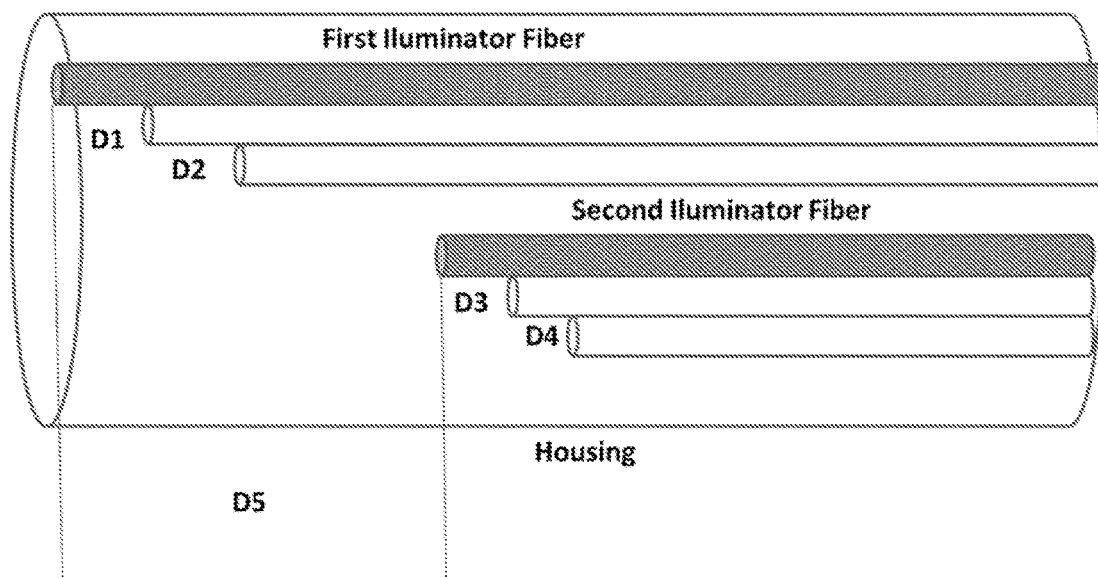
FIG. 8 illustrates an exemplary embodiment of a device with two source detector pairs according to the present disclosure.
Figure 11:
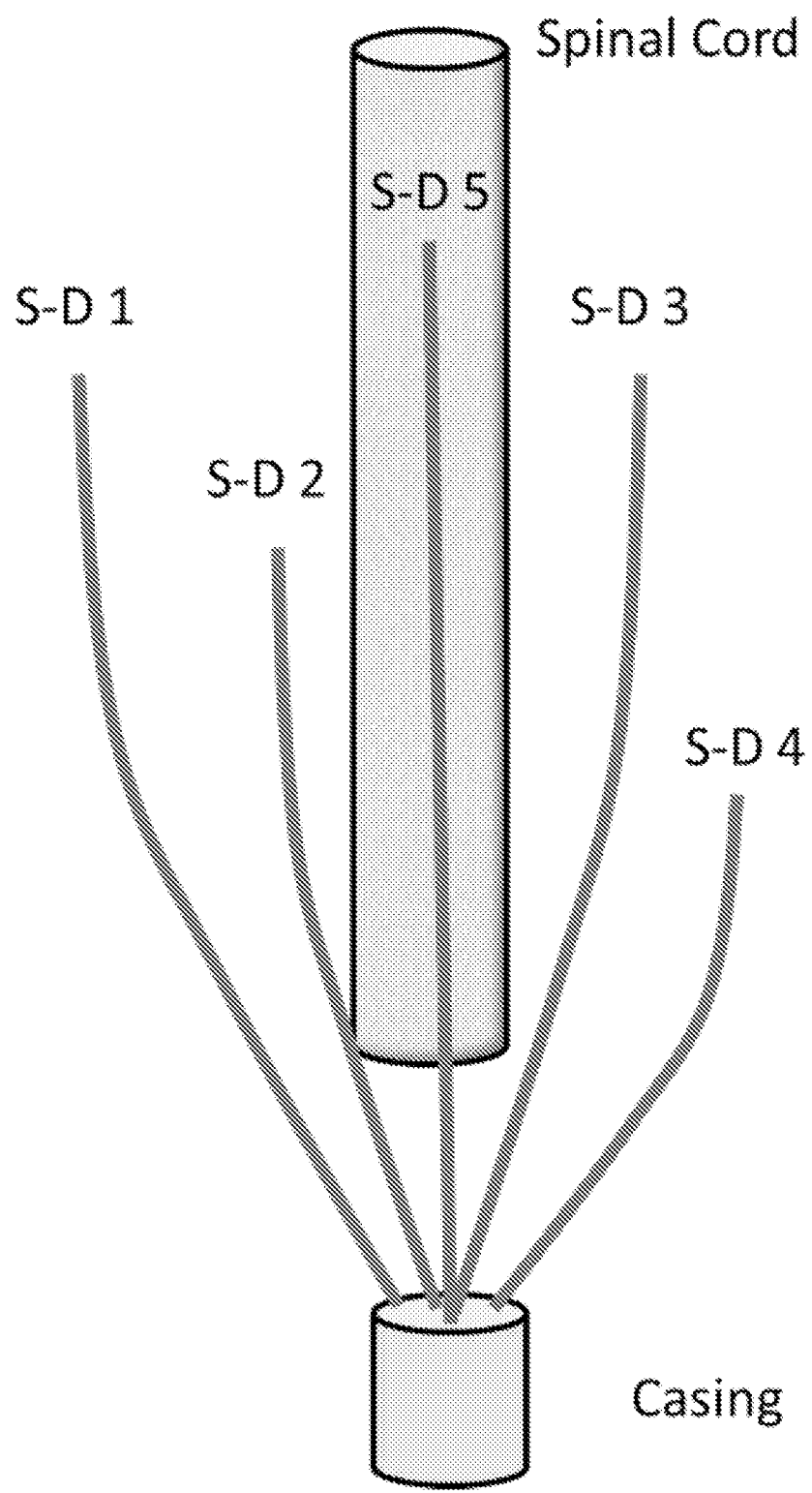
FIG. 11 illustrates a further embodiment of the disclosed devices.

One exemplary device is shown in FIG. 8. As shown in the figure, a housing may have disposed within, a first illuminator fiber and a second illuminator fiber. The first illuminator fiber may be associated with detector fibers, the detector fibers having distal ends that are separated from the distal end of the illuminator fiber by distances D1 and D2. The distances may be in the range of millimeters or even centimeters, depending on the user's needs and the device's configuration. It should be understood that the devices do not require the presence of two detector fibers, as the illuminator fiber may be associated with only a single detector fiber, or may be associated with multiple detector fibers. An exemplary deployment of a device having a source fiber-detector-fiber pairing is shown in FIG. 11, which figure illustrates the presence of the fiber pair in the vicinity of the spinal cord of an animal model.

A device may also include a second, third, or additional illuminator fibers as shown by exemplary FIG. 8. The second illuminator fiber may be associated with detector fibers, the detector fibers having distal ends separated from the distal end of the illuminator fiber by distances D3 and D4. The distances may be in the range of millimeters or even centimeters, depending on the user's needs and the device's configuration. It should be understood that a second illuminator fiber does not require the presence of two detector fibers, as the second illuminator fiber may be associated with only a single detector fiber, or may be associated with multiple detector fibers. As shown in FIG. 8, the distal ends of the illuminator fibers may be separated by distance D5. This separation of the illuminator fibers enables a user to interrogate tissue at two different distances along the length of the probe. In an application where the probe is inserted into the epidural or intrathecal spaces, this enables the user to interrogate the spinal cord at multiple levels, e.g., a lower thoracic region of the patient and also a high lumbar region of the patient. The fibers may illuminate at the same or different wavelengths. In this way, the user may obtain information about two characteristics (e.g., blood flow, blood oxygenation) of two tissue locations.

The devices may incorporate a variety of illumination sources. Lasers, diodes, fluorescent sources, incandescent sources, thermal sources, and the like are all suitable sources of illumination. The illumination source may be configured to provide illumination of a single wavelength, or even of two or more wavelengths, in an alternating or switching fashion. The illumination source may be adapted to provide illumination having a wavelength in the range of between about 1 nm and about 1200 nm, or in the range of from between about 600 nm and about 900 nm, or even in the range of from between 600 nm and about 700 nm.

Illumination, detection, or both fibers are suitably disposed within a housing that is itself suitable for insertion and placement into the epidural space, the intrathecal space, or both. The housing may be a tube or other conduit. Such a housing is suitably transparent or at least partially transparent to the illumination provided by the illumination fiber and illumination collected by detector fibers. The housing may be formed from a polymeric material. Alternatively, illumination and detector fibers may themselves be adapted for placement into the epidural space, the intrathecal space, or both. The housing may include markers or indicia to enable discrimination of positioning by visible or other imaging methods (MRI, radiographic). Such markers may include radiopaque regions, such as stripes or dots, as well as regions that are visually perceptible.

Devices may also include a computer-readable medium having computer-executable instructions. The computer-executable instructions may calculate a correlation function, which correlation function may correlate the illumination gathered by one or more detector fibers to one or more of the characteristics (e.g., blood flow, blood oxygenation) mentioned elsewhere herein. As one illustrative example, oxygen metabolism is measured using a bulk overall technique.

The devices may also include a catheter integrated with the first illuminator fiber and first detector fiber. The catheter may be adapted for use as an epidural, or intrathecal catheter for infusions or for monitoring of pressure. The fibers may be disposed within the lumen of the catheter, or, alternatively, may be disposed on the exterior of the catheter. The fibers may be attached to the catheter at one or more points. A fiber may also be embedded, slotted, or otherwise engaged into an interior or exterior surface of the catheter.

Such catheter-containing devices may be used so as to allow users (e.g., surgeons) to monitor the post-operative progress of a patient. For certain procedures, a patient may receive a catheter used to deliver one or more medications to the patient during or even after an operation for pain control, or the catheter may be used to monitor pressure around the spinal cord and for draining cerebrospinal fluid. In some cases, however, a catheterized patient may develop a hematoma or around the catheter, resulting in spinal cord compression and ischemia. Detection of hematomas or other conditions in such patients can be challenging, however, as such patient are often heavily medicated following surgical procedures and may not be able to advise their caregivers of the discomfort that is normally associated with hematomas, nor allowing for a reliable neurological examination to be performed. Such hematomas can result in acute paralysis and or paresis.

By integrating illuminator and detector fibers with a catheter, the disclosed devices allow a user to deliver medication via catheter or drain via the catheter while also monitoring the patient for changes in physiological characteristics (e.g., changes in blood flow, changes in blood oxygenation) that are indicative of a hematoma, ischemia, or other negative conditions within the patient. The catheters may be standard catheters known to those of ordinary skill in the art. By having multiple illuminator fibers and detector fibers, the user may, as described elsewhere herein, obtain information about multiple tissue locations in and around the catheter so as to assess whether a hematoma or other condition has arisen within the patient.

As described above, the devices may include multiple sets of illuminator (or source) fibers associated with detector fibers. These source-detector sets may, in some embodiments, be placed at different locations along the length of the spinal cord so as to enable the user to obtain information concerning blood flow, oxygenation, or other tissue characteristics along the length of the cord. In another embodiment, shown in illustrative FIG. 9, the source-detector sets may be spread or fanned out across the spinal cord.

Figure 9:
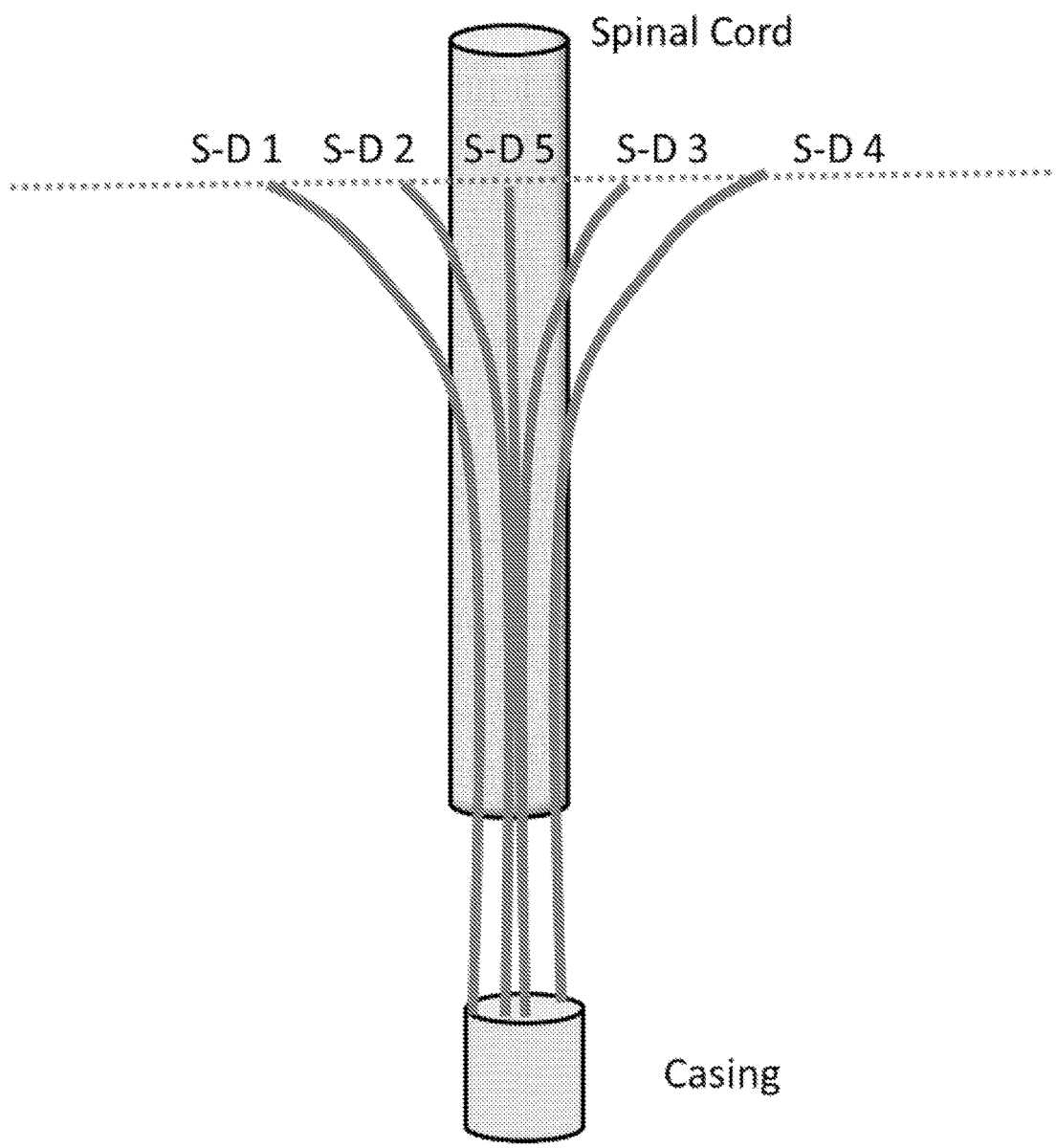
FIG. 9 illustrates an alternative embodiment of the device that features a spread of source-detector pairs.

In FIG. 9 (not necessarily to scale), five source-detector pairs (S-D 1 through S-D 5) are spread across the spinal cord. A detector-source pair may include one illuminator (source) fiber that is in turn associated with one or more detector fibers. The five pairs may be positioned such that their distal ends are roughly in-plane with one another, as shown in the figure by the dotted line. By spreading the source-detector pairs out, one may generate an image (e.g, a two-dimensional image) that represents the presence of oxygenated blood, for example, in a cross-section of the spinal cord. It should be understood that the source-detector pairs may be present at one or more depths. For example, pair S-D1 may lie above the spinal cord, pair S-D2 may lie next to the spinal cord, pair S-D3 may lie under the cord, pair S-D4 may lie next to the spinal cord, and pair S-D5 may lie above the spinal cord. The "casing" shown in the figure is illustrative only and is intended only to show that individual source-detector pairs may, if desired, be bundled in a casing and then be deployed from within that casing.

Figure 10:
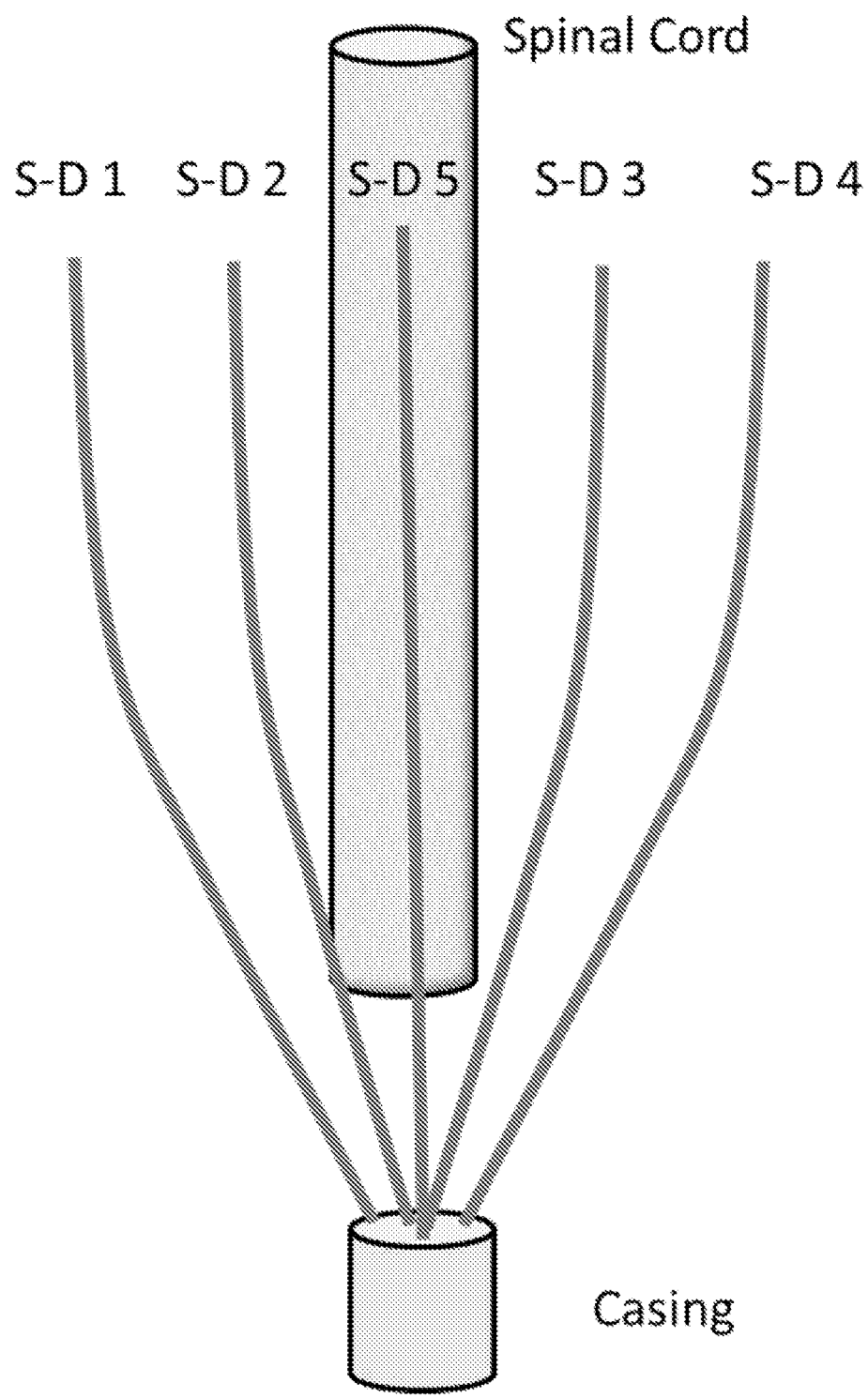
FIG. 10 illustrates an additional, alternative embodiment of the device that features a spread of source-detector pairs.
Figure 12:
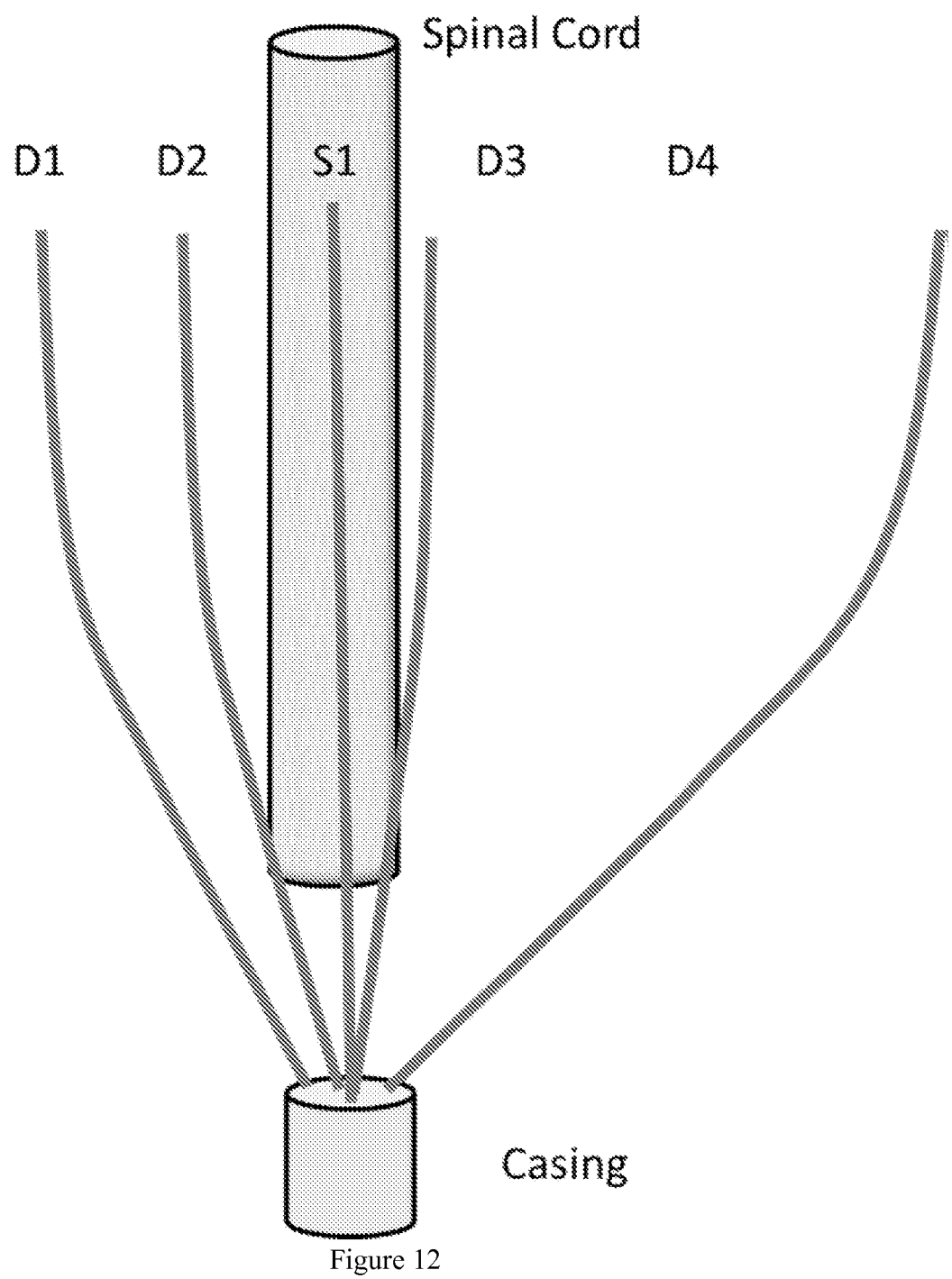
FIG. 12 illustrates another embodiment of the disclosed devices.

FIG. 10 presents an alternative embodiment of the disclosed devices. Source-detector pairs S-D1 through S-D5 are arranged across or even around the spinal cord as shown. This configuration may be characterized as being "rake-like" in its arrangement of source-detector fibers. As described in connection with FIG. 9, the distal ends of the sources and detectors may be in-plane with one another. FIG. 11 presents an embodiment where the distal ends of the sources and detectors terminate at different positions. FIG. 12 presents another embodiment of the disclosed devices wherein the distal ends of detector fibers D1-D4 are present at varying distances from the spinal cord and illumination (source) fiber S1. By spreading the detectors in such a way, the user may obtain data from tissue at different distances from the spinal cord, which data can in turn be combined so as to form a two-dimensional or even three dimensional representation of the condition of a cross-section of the spinal cord.

It should be understood that by changing the illumination supplied by the illuminator fiber, the user may assess more than one characteristic of the tissue being studied. For example, the user may first illuminate the tissue with illumination having a comparatively long coherence wavelength used to assess blood flow. The user may then provide illumination having one or more other wavelengths so as to assess blood oxygenation. In this way, the devices present the capability of assessing multiple tissue characteristics.

The present disclosure also provides methods. These methods include illuminating, with light emitted from the distal end of an illuminator fiber, a first region of tissue proximate to the spinal cord; collecting, with a first detector fiber having a distal end at a distance from the distal end of the illuminator fiber, illumination from the first region of tissue; and correlating the collected illumination to a level of tissue blood oxygenation, a level of tissue oxy-hemoglobin, a level of tissue de-oxy-hemoglobin, a level of tissue blood flow, water content, lipid presence, tracer presence, or any combination thereof.

As described elsewhere herein, the user may also illuminate a second region of tissue proximate to the spinal cord and at a distance from the first region and collecting illumination from the second region of tissue. The distance between the first and second tissue regions may be from 0.1 mm to about 10 cm or even 20 cm.

In some embodiments, the first or second region is upstream (in terms of blood flow) from the other. The user may select the first and second regions so as to obtain information that enables a comparison between, for example, (1) a region that has undergone a surgical procedure, a region that is injured, a region that is suspected of being injured, or some other region of interest and (2) a "control" region that serves as a baseline or normal region. For example, a user may use the fibers to assess the blood oxygenation around the spinal cord at a "control" thoracic region that has not been operated upon with the blood oxygenation around the spinal cord at a lumbar region that has been operated on or that is suspected of being injured. A difference in oxygenation levels between the control and operative regions may indicate to the user that the lumbar region has been damaged and that the user may desire to intervene (e.g., by adjusting the position of an instrument) so as to restore or enhance blood flow to the lumbar region. Alternatively, a user may interrogate tissue at two locations so as to establish baseline levels of blood flow, blood oxygenation, or other characteristic at those locations, which baseline levels may be used to assess the condition of those locations before, during or after a surgical procedure, or in connection an injury.

The first and second regions are suitably separated by a distance from one another. Such distance may be a radial distance relative to the spinal cord, or even an axial distance relative to the spinal cord's major axis. For example, the user may assess tissue at a particular thoracic location that is located at 1 and 2 cm from the device. Alternatively, the user may assess tissue at a thoracic location that is 1 cm from the device and also tissue at a lumbar location that is 1 cm from the device.

A user then suitably correlates illumination collected from the second region of tissue to a level of tissue blood oxygenation, a level of tissue oxy-hemoglobin, a level of tissue de-oxy-hemoglobin, a level of tissue blood flow, or any combination thereof. A user may also correlate the collected illumination to water presence, lipid presence, or even the presence of an exogenous tracer or dye, as described elsewhere herein.

The disclosed methods also include collecting illumination with a second or multiple detector fiber(s). The second detector suitably has a distal end that is at a distance from the distal end of the first detector fiber. The distal ends may be separated from one another by from about 0.1 mm to about 20 cm, or from about 1 mm to about 10 cm, or even from about 2 mm to about 1 cm.

The user may correlate the levels of tissue blood oxygenation, a level of tissue oxy-hemoglobin, a level of tissue de-oxy-hemoglobin, a level of tissue blood flow, or any combination thereof, to a representation of one or more of the foregoing in a cross-section of the spinal cord. As shown by exemplary FIGS. 9-14 and their associated description, illuminator-detector pairs may be positioned about the spinal cord (or other tissue region) so as to obtain tissue characteristic (e.g., oxygenation) data at various locations around or along the tissue. These data may then be combined so as to arrive at a representation (e.g., a two-dimensional image) of the presence of that characteristic within or around the tissue. For example, by placing splayed fibers above, below, and to the sides of a spinal cord, the user may obtain information concerning blood oxygenation in a cross-section of the cord. More specifically, by placing detectors at the 12 o'clock, 3 o'clock, 6 o'clock, and 9 o'clock locations around a particular point on the spinal cord, the user may then obtain, for example, blood oxygenation information at each of those points. This information may then be assembled to provide a representation of blood oxygenation in the cross-sectional slice of the spinal cord.

Figure 13:
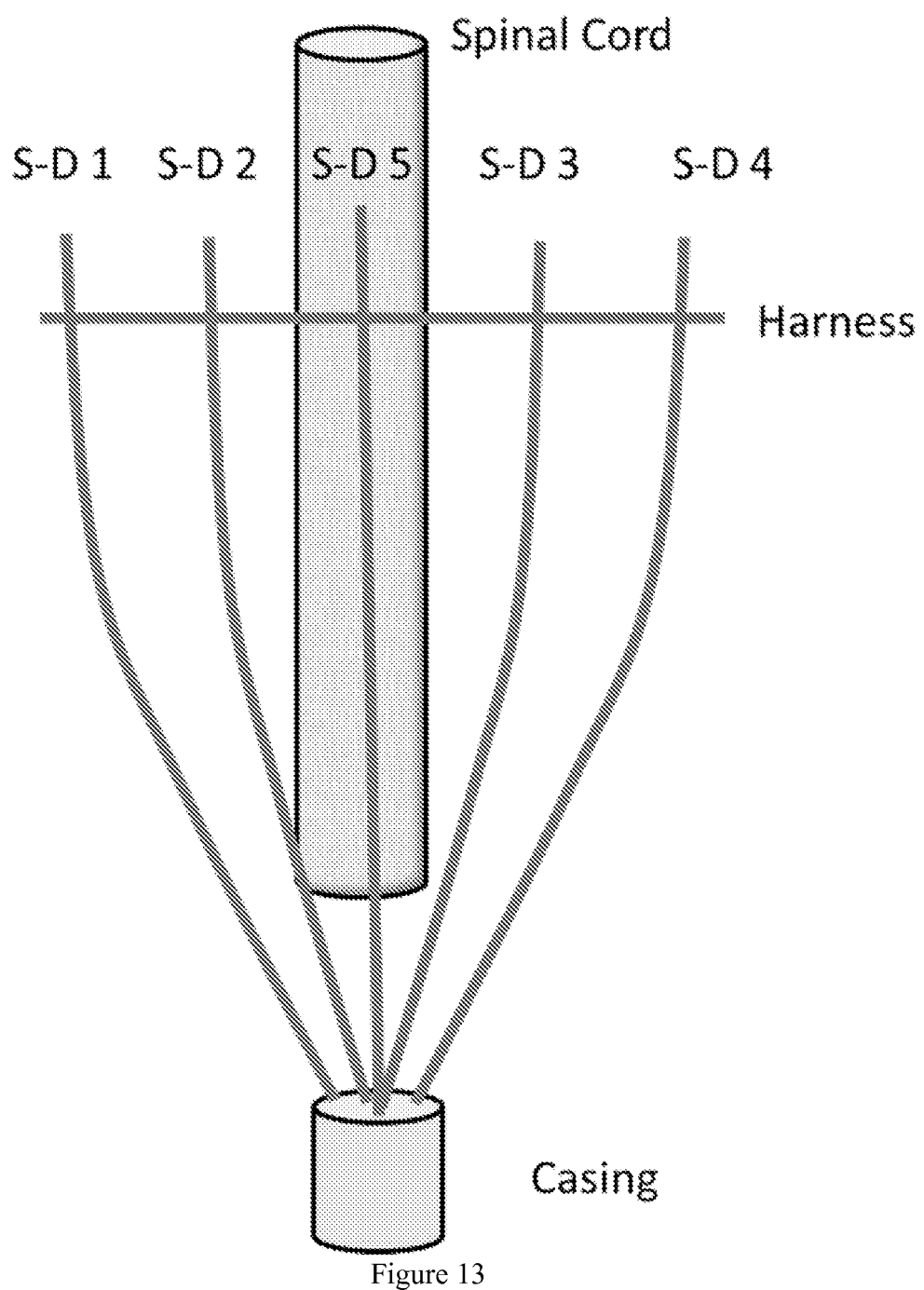
FIG. 13 illustrates the embodiment of FIG. 10 with the addition of a harness connecting the various source-detector pairs.

In some embodiments, such as the embodiment shown in FIG. 13, the device may include a harness (e.g., a brace, strap, or ribbon) that secures two or more separate source-detector pairs to one another. For example, as shown in FIG. 13, the source-detector fibers of FIG. 10 may be connected to one another by a band or other material, which material may be a stiff material. This harness serves to maintain the relative alignments of the source-detector fibers. The connector may be flexible (e.g, be formed from a bendable plastic or even a bendable metal) such that the user may bend the connector and arrange their fibers to accommodate the specific physical characteristics of a subject's anatomy. The harness may be configured such that individual fibers or source-detector sets may be slid into and out of holes or other apertures formed in the harness. The harness may be integral to a source fiber, a detector fiber, or a set thereof, and may be bonded or otherwise affixed to the fibers.

Figure 14:
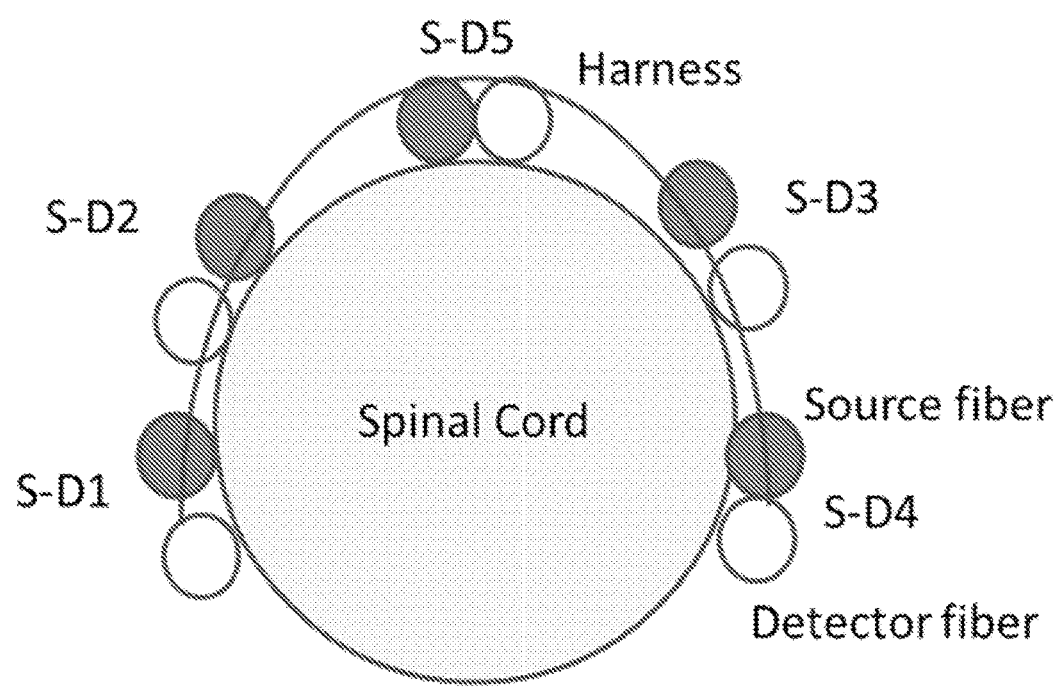
FIG. 14 illustrates a cross-sectional view of the exemplary embodiment shown in FIG. 13.

FIG. 14 shows an illustrative, non-limiting arrangement of five source-detector fiber sets (SD-1 through SD-5) around an exemplary spinal cord, with a harness (which may, as mentioned above, be formed from a bendable material) that maintains the positions of the source-detector sets. As shown in FIG. 14, source-detector pairs may be positioned at the upper face (SD-5) of the spinal cord, at the sides of the spinal cord (SD-1 and SD-4), and between the top and sides (SD-2 and SD-3). These positions shown in the figure are not limiting, as source-detector sets may be positioned at any location around the spinal cord, including at the top and bottom and the two sides. In one embodiment, a user may deploy four source-detector sets that are arranged at 90-degree intervals around the circumference of the spinal cord. A user may use source-detector sets arranged at 120 degree intervals around the circumference of the spinal cord. The arrangement and spacing of source-detector sets may, of course, vary according to a user's particular parameters. It should be understood that although FIG. 14 illustrates source-detector sets that consist of a source fiber (dark-shaded) and a detector fiber (unshaded), source-detector sets may of course include multiple source fibers, multiple detector fibers, or both.

Illumination supplied by the illuminator fiber may be at a single wavelength, or even at two or more wavelengths. A user may apply a single wavelength of illumination to the tissue and then apply a second, different wavelength of illumination to the tissue. A user may use one, two, or more illuminators.

The user may translate the illumination fiber to a second location, illuminating a second region of tissue, collecting illumination from the second region of tissue; and correlating the collected illumination to tissue blood oxygenation, a level of tissue oxy-hemoglobin, a level of tissue de-oxy-hemoglobin, a level of tissue blood flow, or any combination thereof. A user may also correlate the collected illumination to water presence, lipid presence, or even the presence of an exogenous tracer or dye.

A user may also deliver an agent to a subject. The agent may be, for example, a pain medication or other therapeutic. The agent may be delivered intravenously or even by way of a catheter, such as an epidural or intrathecal catheter. The catheter may be integrated with the fiber optic probe (e.g., containing one or more illuminator fiber and/or detector fibers) such that the foregoing components are integrated into a single device. The user may then illuminate the tissue of interest with illumination that is used to visualize or otherwise detect the agent, as described elsewhere herein. The user may then correlate the collected illumination to the level of presence of the agent in the subject.

Devices that present the capability to introduce an agent and to assess tissue condition are also provided. These devices are suitably configured as a fiber optic probe and integrated catheter device. In one embodiment, the devices include an elongate fiber optic probe and integrated catheter devices being adapted for insertion into the epidural space, the intrathecal space, or both. The fiber optic probe and integrated catheter device is suitably integrated with a first illuminator fiber having a distal end. A first detector fiber is also suitably integrated with the fiber optic probe, with the first detector fiber having a distal end located at a first distance from the distal end of the first illuminator fiber. The first illuminator fiber is suitably capable of being in optical communication with an illumination source. Similarly, the first detector fiber is also suitably capable of in optical communication with a first illumination detector. Do we need artwork here?

Suitable detectors are described elsewhere. Such detectors include, e.g., CCD devices, photomultiplier tubes, photodiodes, and the like. The devices may also include a computer processor in communication with the first illumination detector, the computer processor being adapted to estimate, based on illumination received by the first illumination detector, blood oxygenation, oxy-hemoglobin, deoxy-hemoglobin, blood flow, oxygen metabolism, water content, lipid presence, exogenous tracer presence, or any combination thereof.

The present disclosure also presents methods. These methods suitably include illuminating, with light emitted from the distal end of an illuminator fiber integrated with a fiber optic probe, a first region of tissue proximate to the spinal cord; collecting, with a first detector fiber integrated with the fiber optic probe and having a distal end at a distance from the distal end of the illuminator fiber, illumination from the first region of tissue; and correlating the collected illumination to a level of tissue blood oxygenation, a level of tissue oxy-hemoglobin, a level of tissue de-oxy-hemoglobin, a level of tissue blood flow, water content, lipid presence, tracer presence, or any combination thereof, or any combination thereof. The user may administer an agent (e.g., a tracer or dye) to a subject by way of the integrated or independent catheter. The user may correlate the collected illumination to a level of the agent or a reaction product of the agent in the subject. Reaction products include, for example, a metabolic product of the agent. A reaction product may also include the result of the agent's interaction with the subject, such as a calcium-sensitive dye that changes conformation or even binds to calcium. Such a dye may include a fluorescent molecule that is detectable under illumination, or may include a molecule having an absorbance that is detectable under illumination.

The fiber optical devices disclosed here suitably use diffuse optical and diffuse correlation spectroscopic (DOS, DCS) principles, for the real-time and continuous measurement of oxygenation and blood flow in the spinal cord. The devices may consist of multiple, sequential sensors positioned along the length of the device, for the monitoring of flow and oxygenation at multiple levels and depths within the spinal cord. The devices measure flow and oxygen as close to the site of injury as possible, due to its placement within the intrathecal or epidural space, with minimal or no intervening tissue to impair sensitivity, spatial, or temporal resolution. The disclosed device is capable of reporting measurements over multiple spinal cord regions, simultaneously. The device may be placed via open and percutaneous methods and approaches currently in clinical use and with proven safety. The devices are suitably flexible and with high tensile strength to prevent breakage. The material of the devices is suitably inert and does not cause injury or inflammation, even if left in place or fractured.

Optical methods offer a range of sensitivities useful for characterization of a wide variety of samples. One such method is light absorption, whereby attenuation in signal intensity occurs whenever the light wavelength coincides with a material resonance. This effect enables quantitative determination of the molecules present in a sample, their concentration, and their local environment. In a different vein, sample morphology is accessible through light scattering experiments. In traditional single scattering experiments the angular pattern of the collected light intensity provides information about scatterer size, refractive indices of scatterers and background fluids, and the organization structure of collections of scatterers. Finally, fluctuation spectroscopies, including dynamic or quasi-elastic light scattering measure temporal light intensity fluctuations from the sample to gain information about the motions of scatterers. All of these optical spectroscopic techniques are rigorous and well established in simple, homogenous, optically thin samples.

Diffuse optical imaging and spectroscopy aims to investigate tissue physiology millimeters to centimeters below the tissue surface. Light is scattered very strongly in tissue, however, and traditional optical spectroscopies cannot be used for this purpose. Fortunately, a spectral window exists in the near-infrared ("NIR," about 700-900 nm), wherein photon transport in tissues is dominated by scattering rather than absorption. Even in this window, however, one may desire to separate the effects of tissue absorption and internal motion from the effects of tissue scattering. In the limit of high scattering, it is well accepted that light transport is well approximated as a diffusive process. Using this physical model one may quantitatively separate tissue scattering from tissue absorption, and to accurately incorporate the influence of boundaries, such as the air-tissue interface, into the transport theory. Without being bound to any particular theory, due to its intrinsic properties, such as high temporal resolution and the ability to probe deep tissues continuously and noninvasively, diffuse optical methods may be an inexpensive and portable tool for studying spinal cord injuries.

Diffuse optical techniques separate naturally into "static" and "dynamic" methods. The "static" method, which may be called Diffuse Optical Spectroscopy (DOS), is concerned with measurement of relatively slow variations in tissue absorption and scattering. DOS, also known as diffuse reflectance spectroscopy (DRS) or near-infrared spectroscopy (NIRS), has been the most widely applied diffuse optical technique in biomedical research. In DOS, the optical properties of the tissue (i.e., absorption and scattering coefficients) are obtained by collecting the light intensity detected few centimeters away from a NIR light source, after passing through the tissue. The diffuse light measurements useful in the disclosed devices employ intensity modulated light sources (i.e., the frequency domain technique). This approach enables quantitative absolute measurements of the optical properties of tissue.

In some examples of this approach, the amplitude of the input source is sinusoidally modulated, producing a diffusive wave within the medium. The amplitude and phase of the transmitted diffuse light waves are measured as a function of source-detector separation and/or wavelength. One physical model for tissue spectroscopy treats the sample as a semi-infinite medium wherein sources and detectors are placed on the "air side" of the tissue surface. Emission and detection take place through optical fibers placed flush with the surface. Diffusion theory for semi-infinite media predicts the reflectivity, R, as a function of the source-detector separation along the sample surface. R is predicted by the diffusion equation.

Tissue optical properties are then derived by fitting the measured amplitude and phase of the diffuse light reflectivity, R, to the predictions of diffusion theory with specific tissue optical parameters for absorption and scattering. Various schemes have been developed to search for the optimal parameters, and their relative success depends on measurement signal-to-noise ratio and the accuracy of the physical model. The absorption coefficient can be decomposed into contributions from different tissue chromophores, i.e. $\mu_a(\lambda)=\Sigma\varepsilon_i(\lambda)c_i$. Here the sum is over the different tissue chromophores. $\varepsilon_i(\lambda)$ is the extinction coefficient as a function of wavelength for the $i^{th}$ chromophore. $c_i$ is the concentration of the chromophore. The $c_i$ are unknowns to be reconstructed from the wavelength-dependent absorption factors. Three unknowns require measurements at a minimum of three optical wavelengths (generally more, since tissue scattering is also an unknown). Oxy- and deoxy-hemoglobin concentrations (e.g. $c_{HbO2}$, $C_{Hb}$ respectively) along with water concentration are the most significant tissue absorbers in the NIR. Their combination gives total hemoglobin concentration (THC=$c_{Hb}$+$C_{HbO2}$) and blood oxygen saturation ($S_tO_2=c_{HbO2}$/THC×100), both of which are useful physiological parameters.

Dynamic methods monitor the speckle fluctuations of the scattered light, which in turn are sensitive to the motions of scatterers such as red blood cells. In flow experiments, the measured quantity of interest is the electric field temporal autocorrelation function $G_1(r,\tau)=<E(r,t)E^*(r,t+\tau)>$ or its Fourier transform. Here the angle brackets $<>$ denote ensemble averages or averages over time. $\tau$ is called the correlation time. The field correlation function is explicitly related to motions of scatterers within the samples.

The extension of dynamic light scattering to deep tissues was pioneered by Dr. Yodh. The technique, known as Diffuse Correlation Spectroscopy (DCS), aims to quantify the fluctuations of the scattered detected light in deep tissues. Such fluctuations occur due to the motion of scatterers in tissue, mainly red blood cells. Quantitative study of motions in deep tissues is made possible because the electric field temporal autocorrelation function for light traveling in highly scattering media also obeys a diffusion equation. In steady-state and in piece-wise homogeneous media, the correlation diffusion equation is:

$$(D\nabla^2-v\mu_a-\alpha k_0^2\mu'_2\langle\Delta r^2(\tau)\rangle/3)G_1(r,\tau)=-vS(r).$$

Here $k_0$ is the wave-vector of the photons in the medium. $\langle\Delta r^2(\tau)\rangle$ is the mean-square displacement in time $\tau$ of the scattering particles (e.g., blood cells); the mean-square displacement is the primary quantity we measure and attribute to blood flow or changes thereof. S(r) is the source light distribution, and a represents the fraction of photon scattering events in the tissue resulting from moving cells or particles. The correlation diffusion equation can have different forms depending on the nature of the particle motion, and on the variations of these motions with position in the sample. For example, the mean-square displacement $\langle\Delta r^2(\tau)\rangle=6D_B\tau$ for cells undergoing 'effective' Brownian motion with diffusion coefficient $D_B$.

Without being bound to any particular theory, blood flow may be derived from the fit of the measured temporal decay of the diffuse light intensity temporal autocorrelation function to the solution of the diffusion model for the electric field temporal autocorrelation. The Siegert relation provides the relationship between the electric field temporal autocorrelation function and the light intensity temporal autocorrelation function. In principle, DCS can measure absolute levels of blood flow. In practice, however, it is desirable to calibrate DCS with other measurement techniques. In this disclosure is presented continuous monitoring of relative changes of blood flow in the spinal cord. The technique has been extensively validated during the last few years, both in animals and in humans. DCS-blood flow measurements have been compared with perfusion measurements acquired with arterial spin-labeled MRI, Xenon-CT, laser Doppler flowmetry, and transcranial Doppler ultrasound. The technique has been successfully applied in to the study of cerebrovascular diseases, muscle physiology, and tumor physiology.

DCS shares all the features of DOS, including portability, non-invasiveness, and the ability to probe deep tissues. However, DCS also provides a qualitatively different physiological signal. In DOS, the signal is related to the hemoglobin concentration changes via optical absorption. By contrast, the DCS signal is due to the motion of scatterers in the tissue. Because no significant cross-talk between DOS and DCS has been observed, the techniques can be combined to provide continuous relative measurements of both blood flow and tissue oxygenation.

Devices combine photon correlation (DCS) technology, for studies of tissue internal motions, and diffuse photon wave spectroscopic (DOS) tools, for studies of tissue absorption and scattering. This hybrid multi-channel, portable instrument may investigate blood flow and blood oxygenation in tumors, in muscle, in rat brain, and in human brain. All-optical devices may thus extract regional information about flow and blood oxygenation in deep tissue. A description of exemplary modules is given below.

DCS Component:

An exemplary DCS module uses narrowband, continuous wave, diode lasers, in the near-infrared range (typically 785 nm), with comparatively long coherence length (>20 m) as the light source (CrystaLaser inc., NV). The light beam is delivered to the tissue through an optical fiber, with an output power of approximately 5-15 mW. Light intensity fluctuations within a single speckle area are detected using a single-mode fiber detection and fast single photon counting devices, such as avalanche photo-diodes (PerkinElmer, Canada). Finally, an autocorrelator (Autocorrelator.com, NJ) is used in the measurements. The autocorrelator takes the detector output and uses photon arrival times to compute the light intensity temporal autocorrelation function.

Figure 7:
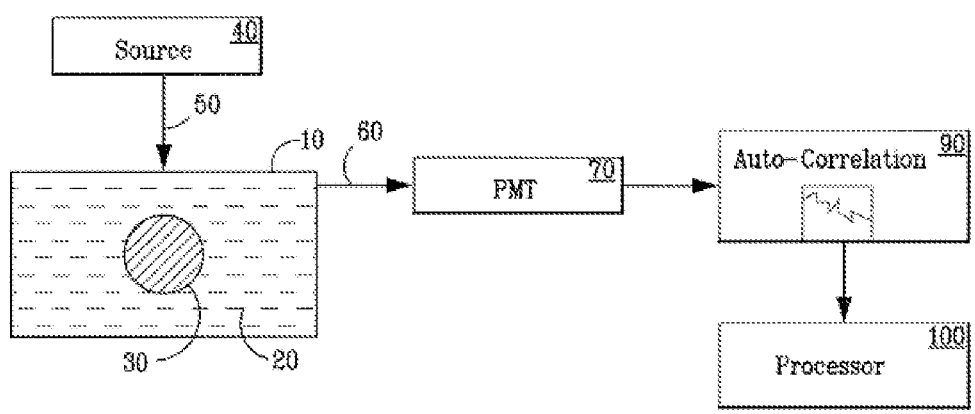
FIG. 7 illustrates a block diagram of an exemplary system for imaging turbid media with spatially varying dynamic properties or spatially varying optical properties.

An exemplary system is shown in FIG. 7. Referring now to the drawings wherein like reference numerals refer to like elements, FIG. 7 is a block diagram of an exemplary system for imaging media having spatially varying dynamic properties or spatially varying optical properties.

A turbid medium is shown generally at 10, and comprises a substantially heterogeneous matrix 20 wherein there is embedded an object 30. The object 30 contains small particles which are moving in a non-ordered fashion. "Non-ordered fashion" means that the particles exhibit Brownian motion, turbulent motion, shear flow, random motion, velocity changes or any other motion which results in a change in the relative distance between the particles. In an experimental setup, the matrix 20 is a solid slab of titanium dioxide suspended in resin, and the object 30 is a small cavity with a 0.2 percent suspension of 0.296 micrometer diameter polystyrene spheres. The slab has dimensions of 15×15×8 centimeters.

A source of light 40 is coupled by a multimode fiber 50 to the medium 10. Preferably, the source 40 is a coherent source of energy. Even more preferably, the source is a laser or a stable light source, well known to those skilled in the art. The source may be, for example, an argon ion laser that outputs energy in the 514 nanometer green wavelength range.

A fiber 60 is placed at a known position with respect to the matrix 20, and detects light that diffuses through the medium 10. A detector 70 is interfaced to the fiber, and by standard gain techniques creates a signal which is representative of the intensity fluctuations at the fiber resulting from the photons which have diffused through the medium 10 and which may have scattered from the particles in object 30. Any detector which can produce a gain, for example a photomultiplier tube ("PMT"), can be interfaced with the fiber 60, and it will be recognized by those with skill in the art that a fiber-detector combination will produce results in accordance with the invention. It should be understood that an avalanche photodiode ("APD") or other suitable device or devices may also be used in place of a PMT. A suitable fiber for fiber 60 is a single mode fiber.

In accordance with the present invention, a digital autocorrelator 90 is interfaced with the photomultiplier tube 70 in order to observe the intensity fluctuations of the signal speckle. The digital autocorrelation device 90, which is a well-known electronic system that is commercially available, measures the temporal intensity autocorrelation function of the photons received by the detector. As will be described in more detail below, this autocorrelation function can be used to obtain the scattering, absorption and dynamic characteristics of the medium in accordance with the methodology described herein.

Autocorrelation functions may be measured with the source and collecting fibers individually positioned at different locations with respect to the object 30. A computer processor 100 with appropriate software that implements the correlation diffusion theory described below determines the scattering, absorption and dynamic characteristics of the medium from the diffusion correlation wave and thereby reconstructs an image of the dynamically heterogeneous medium 10. Also, the computer may include software that allows a calculation of a correlation function. The computer can be any known, standard processor which can utilize the correlation information output by the autocorrelator 90. In this manner, a reconstructed image of the medium 10 having the object 30 therein can be produced as a function of the scattering and absorption of the diffuse correlation wave as it propagates diffusing through the medium 10.

Transmission and remission measurements of diffuse light intensity emerging from heterogeneous turbid media can provide adequate information for the construction of low resolution images of the spatially varying absorption and scattering coefficients. When the medium is dynamic, the time-dependent density fluctuations of the sample are impressed upon the temporal behavior of the diffusing light. For homogeneous fluctuating turbid media, the temporal intensity autocorrelation function of an emerging speckle of diffuse light can be analyzed to provide information about the temporal fluctuations within the sample. This is the technique may be known as diffuse correlation spectroscopy. Just as diffuse photon density waves can be used to probe the spatial variations in absorption and scattering coefficients within heterogeneous media, position-dependent measurements of the temporal autocorrelation function of diffusing light fields can be used to generate images of temporal fluctuations within heterogeneous turbid media. These techniques may provide a new contrast mechanism for imaging within turbid media.

DOS Component:

One may employ the frequency-domain technique for DOS measurements because it has the capability to provide absolute measurements of the optical properties of tissue. An exemplary system includes three to five diode lasers in the near-infrared range (typically, 685-830 nm), modulated at high frequency (70-110 MHz) by a 1×8 RF splitter (ZFSC-8-1, Mini-Circuits, NY). The output light from the lasers goes through two optical switches (DiCon, CA) before travelling through the source fibers. The first switch ensures that only one wavelength is delivered at a time, while the second helps direct the light to different positions on the spinal cord. The signal from the tissues may be detected either by fast avalanche photodiodes (APD, C5331-01, Hamamatsu, Japan) or photomultiplier tubes (PMT, R928, Hamamatsu, Japan). An in-phase/quadrature (I/Q) demodulator (MIQY-70D; Mini-Circuits, NY) extracts the amplitude and phase information from the RF signal. Low pass filters of 100 Hz on each channel and a 16-bit analog-to-digital converter board (PCI-6032E, National Instruments, TX) are used for data acquisition.

Optical Probe Geometry:

The layout of sources and detectors on the tissue surface defines the optical geometry. Spatial resolution depends on the number of lasers and detectors in the instrument and the combination of each source-detector pair. The depth probed depends on the distance between each source-detector combination, and it is roughly one-half to one-third of the source-detector distance. Additional background is provided in U.S. patent application Ser. No. 11/106,390, "Optical Measurement Of Tissue Blood Flow, Hemodynamics And Oxygenation" (filed Apr. 13, 2005), the entirety of which is incorporated herein by reference for all purposes.

An optical fiber/fiber bundle may be linked to sources/detectors. For sources and DOS detectors, optical fiber bundles with diameters in the range of from about 0.01 mm to about 5 mm are considered suitable as such fibers present a favorable signal-to-noise ratio (SNR). Single-mode fibers (typically 5 um diameter) may be used for DCS detection. For spinal cord monitoring, the low SNR of DCS does not pose a problem given the relatively small dimensions involved. One approach to monitor a region of the spinal cord is to use a shared source for both DCS/DOS and two detectors for each technique, providing two different source-detector separations (FIG. 1).

A thin, flexible, fiber optical probe may be used, which is capable of measuring spinal cord blood flow and oxygenation. The device allows for earlier and accurate detection of spinal cord ischemia than currently available methods. The device may be placed via open or via percutaneous approaches and safely and measures spinal cord flow and oxygenation for several days in an intact, awake animal model.

Percutaneous and open approaches for the placement of the fiber optic probe or fiber optic probe-integrated catheter device near or upon the spinal cord may be used, applying existing approaches for placement of catheters for pain management, anesthetics, and cerebrospinal fluid pressure management. These procedures are accompanied by a high safety profile and are well accepted. These devices present placement of a fiber optical DCS/DOS probe upon, or exquisitely close to, the spinal cord, to allow for the measurement of blood flow and oxygenation.

One may discriminate flow between the anterior versus posterior spinal cord (depth-profile resolution), as the circulations are to a large degree independent. The spinal cord is supplied with blood from two circulations, the anterior and posterior, with some degree of overlap between the two. The anterior circulation originates from the two vertebral arteries superiorly, eventually joining to provide a single anterior spinal artery that runs caudally. The anterior spinal artery supplies ca. 70% of the spinal cord, to include the anterior corticospinal, lateral spinothalamic, anterior one-half of the posterior tracts, the anterior gray matter, and the anterior portion of the posterior gray matter. As the single anterior spinal artery descends it acquires supplemental flow from intercostal and lumbar radiculomedullary arteries. Between the levels of T9 to L5, the arteria radicularis magna (ARM) or artery of Adamkiewicz, originates from the aorta and joins the anterior spinal artery. The ARM is located below T12 in ≈70% and between L1 and L3 in 65% of individuals. At this junction with the ARM, the anterior spinal artery narrows, and it appears that the anterior spinal cord below this point receives the majority of its flow from the ARM. Two posterior spinal arteries also receive their flow superiorly from the vertebral arteries, supplying the posterior half of the posterior gray matter and posterior aspects of the posterior columns. The contribution of collateral flow to the anterior circulation may be critically dependent upon mean arterial pressure when the primary blood supply has been compromised by surgery or trauma. Loss of flow to the anterior cord is associated primarily with motor dysfunction (paresis and paralysis) while impairment in the posterior circulation may result in somatosensory dysfunction (touch and proprioception).

Various scenarios exist where the approach to probe placement may differ. For the removal of a spinal cord tumor, or for a multi-level spinal fusion, a surgeon may desire to place the probe directly into the opened epidural or subdural space after laminectomy. In many cases, such as the monitoring of the spinal cord after trauma, or for vascular procedures, the preferred approach may be to place the fiber optic probe via a percutaneous approach, into the epidural or intrathecal space. The probe is suitably placed without injuring the spinal cord, and is suitably removed intact. The probe allows for safe and reliable acquisition of data over several days in the intensive care setting.

Real-time continuous bedside monitoring renders the devices clinically useful. Currently, final data analysis is performed off-line, partially due to the fact that data processing is computationally high and time consuming, but computing methods are in existence to allow for final analysis to occur at the bedside and will be adapted for this device.

Spine trauma, as a result of motor vehicle accidents, falls, violence, and sports activities, is a global problem in the civilian world also. Rates vary from 12-60 cases/million individuals, with annual costs in the United States approaching $10,000,000,000/yr. Sources of blunt trauma include motor vehicle accidents, blast injuries improvised explosive devices (IEDs), falls, parachute related accidents, aviator crashes, and ejections. Of those with spine injuries (fractures without neurological deficit), one quarter suffer spinal cord injuries. Many of with isolated spine injuries will ultimately require spine stabilization procedures to prevent spinal cord injury. Many patients, adult and pediatric, suffer neurological injury secondary to vascular procedures, resection of spinal cord tumors, and as a result of attempts at the correction of spinal deformities. In addition to the high associated mortality, spinal cord injury is associated with a marked decrease in life expectancy, loss of quality of life and disability. Long-term care costs related to these injuries are staggering.

The disclosed devices have broad application to the management of spine and spinal cord injuries in both acute and subacute settings. Such a device is highly portable allowing and assisting in earlier diagnosis and injury stabilization. This device also has utility in secondary or tertiary centers where it may be used in spine surgery to monitor spinal ischemia during mechanical stabilization procedures. Such devices may aid in the surgical management of patients experiencing aortic injuries, or in the management of patients with aortic aneurysms in need of repair or stenting. The thin fiber optical fiber optic probe may also remain in place for days to allow for the monitoring of injury recovery or progression in the intensive care unit. Lastly, such devices may be used to assist in research efforts in this arena by monitoring the efficacy of interventions upon blood flow and oxygenation.

Illustrative Results

FIGS. 2a-h describe the results of an experiment in an anesthetized and ventilated Dorsett sheep, where a DCS/DOS fiber optic probe with multiple source detector separations (0.5, 1.0, 1.5, & 2.0 cm) was placed upon the dura (epidural) under direct vision after a two level lumbar laminectomy. Information from such a probe assists in optimizing source detector separations and ultimately spatial resolution. During all studies, femoral and carotid arterial pressures were continually monitored invasively. A femoral balloon catheter was placed in the left femoral artery and advanced to a level just below the common cephalic trunk, in the proximal descending thoracic aorta. Hypertension was elicited via bolus of phenylephrine (400 µg), hypotension was elicited via bolus of sodium nitroprusside (400 µg), aortic blood flow was interrupted via inflation of the intra-aortic balloon, and systemic hypoxia and hypercarbia were elicited via temporary respiratory arrest. Percent change in blood flow can be seen on the left y-axis, time is depicted along the x-axis, and mean femoral and carotid arterial pressures are depicted along the right-y-axis.

Figures 2A, 2B:
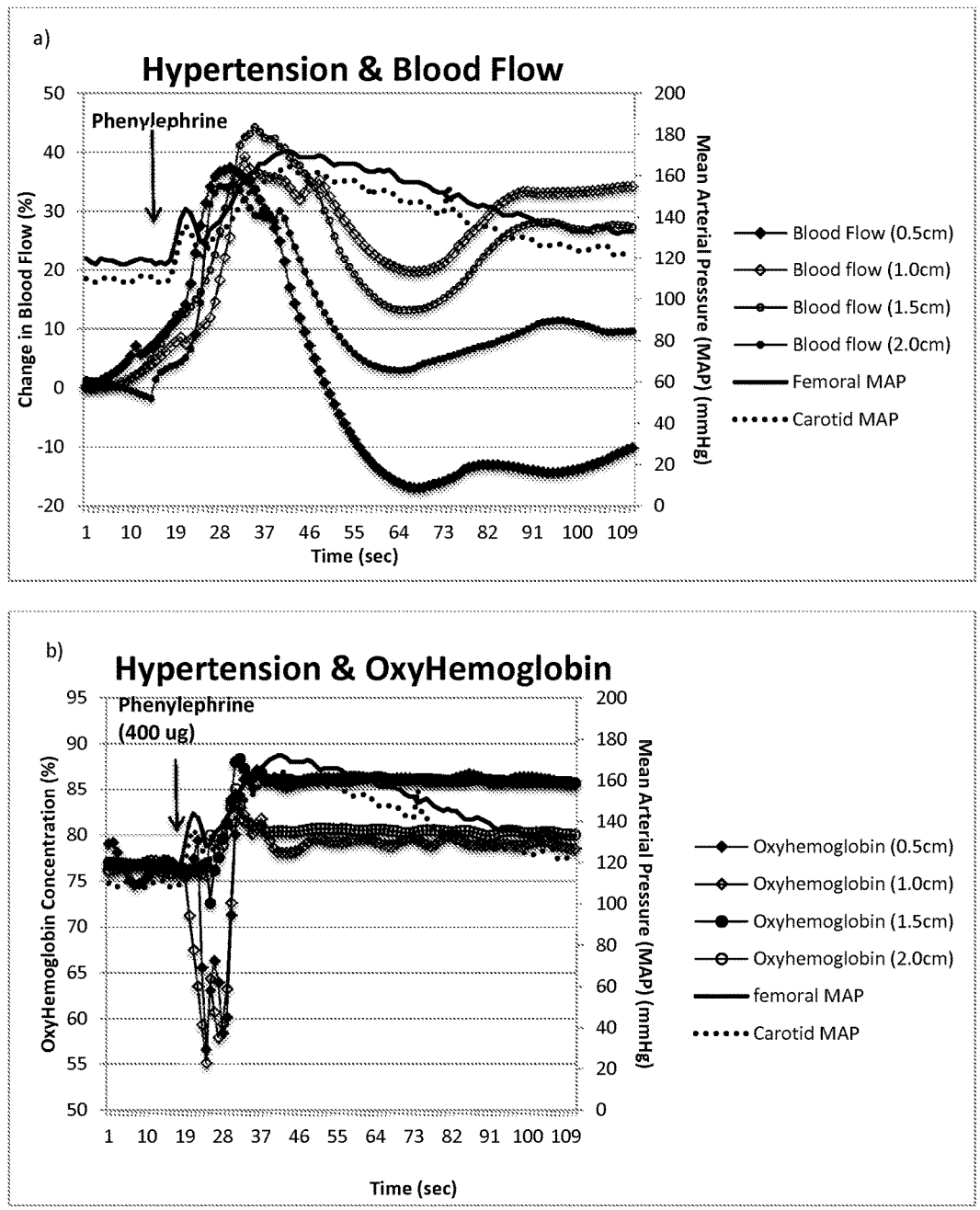
FIG. 2(a-f) presents results of studies in an anesthetized and ventilated Dorsett sheep, where a DCS/DOS fiber optic probe with multiple source detector separations (0.5, 1.0, 1.5, & 2.0 cm) was placed upon the dura (epidural) under direct vision after a two level lumbar laminectomy. Information from the probe may be used to optimize source-detector separations and ultimately spatial resolution.

In FIGS. 2a and b, it can be seen that the probe immediately detected an increase in spinal cord blood flow and oxyhemoglobin levels in response to the acute hypertension elicited by the bolus of phenylephrine (400 ug).

In FIGS. 2c and d, modest hypotension created by the bolus of sodium nitroprusside resulted in a modest decrease in blood flow and oxyhemoglobin.

In FIGS. 2e and 2f, balloon occlusion of aortic blood flow resulted in an immediate drop in femoral blood pressure and rise in carotid blood pressure measured above the intra-aortic balloon. The fiber optic probe detected an immediate fall in spinal cord blood flow and slower fall in oxygenation, consistent with spinal cord ischemia.

Systemic hypoxia and hypercarbia resulted in a divergent increase in spinal cord blood flow and fall in oxygenation, consistent with physiologic expectations.

Next are presented data in FIG. 3(a-d) from a linearly arrayed, clinical fiber optic device, with a single source and two detectors, as is depicted in FIG. 1. The probe was introduced into the epidural space via lumbar laminectomy and advanced cephalad under fluoroscopic guidance. Spinal cord blood flow and oxygenation responses to intra-aortic balloon occlusion were measured at multiple levels. In FIG. 3(a-d), data are presented from two thoracic levels, T-6 and T-9. At each level it can be seen that the probe immediately detected a fall in blood flow commensurate with aortic occlusion, while oxyhemoglobin levels in the spinal cord also fell, but more slowly.

In a separate set of experiments (data not pictured), blood flow data was obtained with the same linear device fiber optic probe, placed under direct vision, into two positions: 1) below the dura (intrathecal) and 2) above the dura within the epidural space. Finally, the probe was placed percutaneously into the subdural space, through a 14 gauge Touhy needle positioned in the lumbar spine, and then easily advanced caudally into the thoracic region. At each position was performed controlled pharmacological (phenylephrine-400 µg, vasopressin-4 units, nitroprusside-400 µg, and nicardipine-2 mg) and aortic occlusions designed to perturb spinal cord blood flow. Blood flow responses from subdural, epidural, and percutaneously placed probes were indistinguishable, indicating that the presence of the intervening dural layer, nor percutaneous placement, impaired the ability of the probe to measure changes in spinal cord blood flow.

Lastly compared were spinal cord blood flow measurements made with the linearly arrayed clinical device, with measurements made with fluorescent microspheres. Colored microspheres were injected into the left atrium to achieve baseline measurements, and then followed by measurements during an intravenous bolus of the hypertensive agent phenylephrine (400 µg), as well as during intra-aortic occlusion. At experimental conclusion, the spinal cord was resected and samples from immediately above and below the fiber optic probe position were retrieved for quantitative microsphere counts/gram tissue.

Figure 4:
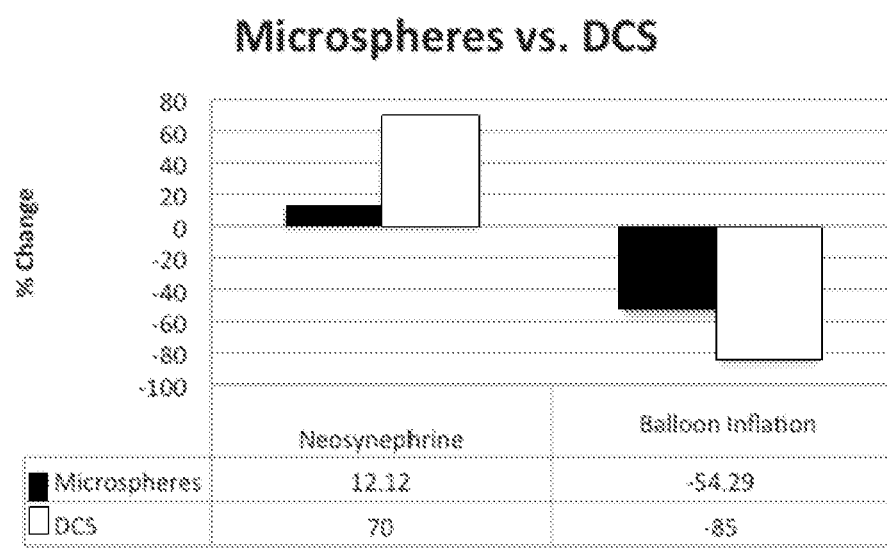
FIG. 4 depicts the results of spinal cord blood flow measurements made with the linearly arrayed clinical device compared with measurements made with fluorescent microspheres.
Figure 5:
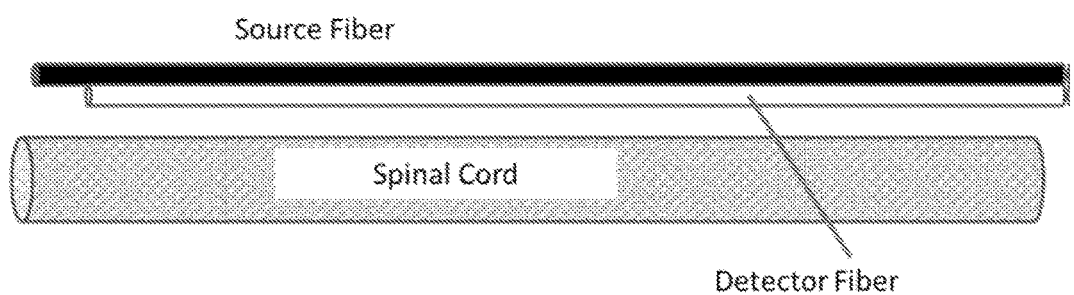
FIG. 5 depicts an exemplary deployment of a source-detector pair according to the present disclosure.
Figure 6:
FIG. 6 presents the position of proximal descending thoracic aortic balloon.

It can be seen in FIG. 4 that the direction of the measurements made with microspheres agreed with measurements made by the fiber optic probe, although the relative magnitude measured differed in favor of the fiber optic probe. Microsphere measurements measure only a single point in time, and this may or may not represent the peak change in flow. The fiber optic probe described herein, has excellent temporal resolution, allowing for the continuous measurements of flow, by sampling once every 200 nanoseconds.

Spatial (In-Depth) Resolution:

As the posterior and anterior spinal cord may be supplied by relatively distinct blood flow sources, one may discriminate changes in blood flow and oxygenation between them.

To achieve this, one may use information from two or more different source-detector distances. The signal from each source-detector pair may be used independently or combined. In the first approach, one may analyze the data from the two source-detector distances independently and assuming a semi-infinite medium. A weighted-regression model may be used to estimate the changes in the two arteries based on the changes in each source-detector separation. The weighted coefficients are obtained with Monte Carlo simulations of photon transport in the spinal cord, with and without priors (e.g., the use of anatomical information of each animal as the propagating medium). In the second approach one incorporates the analytical solution of light diffusion in a two-layer medium to fit the data. More specifically, one adds one more degree of freedom in the model by assuming the propagating medium as a combination of two different layers with different optical and dynamic properties. The fit of the data from all source-detector combinations to the disclosed two-layer analytical model provides blood flow and oxygenation in both layers simultaneously. The thoracic spinal cord in the 30-40 kg sheep has been measured at approximately 1.0 cm. From a two-layer perspective, one may assume (without being bound to any single theory) that the anterior cord would be interrogated at a depth of ≈0.3-0.6 cm, while the posterior cord would be sampled at a depth of ≈0-0.3 cm (and again, at a depth of 0.6-1.0 cm) from the spine. Therefore, the properties of the top (bottom) layer can be attributed to the posterior (anterior) artery.

One may divide acquisition and analysis steps into different processing modules coupled to a PC. The PC (and the user) may have meta-controls over every aspect of the measurement, ranging from communication with modules to measurement control to processing of meta-reconstruction algorithms. The PC may instruct the modules to collect optical data and perform further calculations on the processed data from the modules. It may then carry out a series of computations of increasing complexity to derive tissue optical property maps, chromophore concentration maps and blood flow maps for all the source-detector separations.

DOS Module:

A DOS module allows the user to choose the sample geometry or to input anatomical images to generate the forward model of light propagation. A first sub-unit may perform fast Monte Carlo simulations to determine the contributions of each tissue layer to the measured optical signals, and that are used for estimating the weighted coefficients of the regression model and/or for initializing the initial parameters of the two-layer model. After DOS acquisition by another sub-unit, the inverse problem (i.e., the fit of both the amplitude and phase of the detected light to the chosen model) may be solved to get the optical properties. This procedure may be performed for all source-detector maps. Concentration changes may be determined from the absolute optical properties, and the distribution of the source-detector distances may be used to output a spatial-temporal topographic map to the user.

DCS Module:

The optical properties determined by the DOS module may be used as input to a DCS processing module, after the DCS acquisition task performed by a DCS sub-unit. The DCS inverse problem may be done by an exclusive module.

Auxiliary Module:

One may couple an external acquisition board to the instrument so that data from auxiliary monitoring instruments (e.g., blood pressure monitors, vital monitors, LDF and temperature systems) can also be acquired and controlled in the same environment of the optical fiber instrument. One may use a dedicated module to control, process and output external data.

Central Unit Module:

Each module has an embedded computer to control data acquisition and calculations, and the central unit module is coupled to all modules to control and assess their output. User-friendly screen software may be used to interact with the user, and display the results in real-time. Raw data and processed data may also be saved as spreadsheet file formats that could be uploaded in any data analysis software, such as Excel, Numbers, Origin, or MatLab.

It should be understood that although certain embodiments of the disclosed devices and methods are illustrated by application to the spinal cord, the disclosed devices and methods are not limited to spinal cord applications, and may be applied to other regions of a subject, such as for the monitoring of flow and oxygenation within surgically created vascularized tissue flaps.

What is claimed:

1. A device, comprising:
a first illuminator fiber having a longitudinal axis and having a distal end;
a first detector fiber having a distal end;
a tubular housing having a distal end, the tubular housing at least partially enclosing the first illumination fiber and the first detector fiber,
wherein the distal end of the first detector fiber is at a different location, as measured along the longitudinal axis of the first illuminator fiber, than the location of the distal end of the first illuminator fiber
the first illuminator fiber being in optical communication with an illumination source configured to supply illumination from the first illuminator fiber at from about 600 nm to about 970 nm,
the first detector fiber being in optical communication with a first illumination detector, and
the device being adapted for insertion into the spinal epidural space, the spinal intrathecal space, or both of a subject.

2. The device of claim 1, further comprising a computer processor in communication with the first illumination detector, the computer processor being adapted to estimate, based on illumination received by the first illumination detector, blood oxygenation, oxy-hemoglobin, deoxy-hemoglobin, blood flow, oxygen metabolism, water content, lipid presence, tracer presence, or any combination thereof.

3. The device of claim 2, wherein the computer processor is adapted to estimate blood flow, based on illumination received by the first illumination detector.

4. The device of claim 3, wherein the computer processor is adapted to estimate blood flow at a tissue depth of up to 2 cm, based on illumination received by the first illumination detector.

5. The device of claim 2, wherein the computer processor is adapted to estimate blood flow based on illumination received by the first illumination detector.

6. The device of claim 1, further comprising a second detector fiber, the second detector fiber having a distal end located at a different location, as measured along the longitudinal axis of the first illuminator fiber, than the location of the distal end of the first illuminator fiber.

7. The device of claim 6, wherein the second detector fiber is in communication with the first illumination detector.

8. The device of claim 6, wherein the distal end of the first detector fiber is located at a different location, as measured along the longitudinal axis of the first illuminator fiber, than the distal end of the second detector fiber.

9. The device of claim 8, wherein the distal end of the first detector fiber and the distal end of the second detector fiber are separated, as measured along the longitudinal axis of the first illuminator fiber, by a distance in the range of from about 0.1 to about 20 cm.

10. The device of claim 1, wherein the distal end of the first detector fiber and the distal end of the first illuminator fiber are separated from one another by from about 0.01 to about 20 cm, as measured along the longitudinal axis of the first illuminator fiber.

11. The device of claim 1, wherein the illumination detector comprises a photodiode, an avalanche photodiode, a photomultiplier tube, a CCD camera, or any combination thereof.

12. The device of claim 1, further comprising a third detector fiber having a distal at a different location, as measured along the longitudinal axis of the first illuminator fiber, than the location of the distal end of the first illuminator fiber.

13. The device of claim 1, further comprising a second illuminator fiber, the second illuminator fiber having a longitudinal axis.

14. The device of claim 13, wherein the second illuminator fiber supplies illumination that differs in wavelength from illumination supplied by the first illuminator fiber.

15. The device of claim 13, wherein the second illuminator fiber has a distal end located at a different location, as measured along the longitudinal axis of the first illuminator fiber, than the location of distal end of the first illuminator fiber.

16. The device of claim 15, further comprising a second detector fiber, the second detector fiber comprising a distal end at a different location, as measured along the longitudinal axis of the second illuminator fiber, than the location of the distal end of the second illuminator fiber.

17. The device of claim 1, wherein the illumination source comprises a laser.

18. The device of claim 1, wherein the illumination source is configured to provide illumination at two or more wavelengths.

19. The device of claim 1, wherein (a) the distal end of the first illuminator fiber and the distal end of the first source fiber extend beyond the distal end of the tubular housing or (b) the distal end of the first illuminator fiber and the distal end of the first source fiber are enclosed within the tubular housing.

20. The device of claim 19, wherein the housing has a diameter of up to about 5 mm.

21. The device of claim 20, wherein the housing has a diameter of up to about 2 mm.

22. The device of claim 21, wherein the housing has a diameter of less than about 1 mm.

23. The device of claim 19, wherein one or both of the distal end of the first illuminator fiber and the distal end of the first detector fiber is disposed within the tubular housing.

24. The device of claim 1, wherein the first illumination fiber, the first detector fiber, or both is adapted for placement in the spinal epidural space, the spinal intrathecal space, or both.

25. The device of claim 1, further comprising a computer-readable medium having computer-executable instructions, wherein the computer-executable instructions calculate a correlation function.

26. The device of claim 1, wherein oxygen metabolism is measured using a bulk overall technique.

27. The device of claim 1, wherein the illumination source is adapted to provide illumination having a wavelength in the range of between about 600 nm and about 900 nm.

28. The device of claim 27, wherein the illumination source is adapted to provide illumination having a wavelength in the range of between about 600 nm and about 700 nm.

29. The device of claim 1, the device further comprising a fiber optic probe integrated with the first illuminator fiber and first detector fiber.

30. The device of claim 1, wherein the device is adapted for insertion into the subdural space of a subject.

31. The device of claim 1, wherein the device is configured to interrogate tissue at a depth of up to about 2 cm from the first illuminator fiber.

32. The device of claim 1, wherein the device is adapted for insertion through a needle into a subject.

33. The device of claim 1, wherein one or both of the distal end of the first illuminator fiber and the distal end of the first detector fiber is capable of direct optical communication with a tissue of a subject.

34. The device of claim 1, wherein the distal end of the first illuminator fiber and the distal end of the first detector fiber are in direct optical communication with one another.

* * * * *